US012595293B2

(12) United States Patent (10) Patent No.: US 12,595,293 B2
Perales-Puchalt et al. (45) Date of Patent: Apr. 7, 2026

(54) ANTI-FOLLICLE STIMULATING HORMONE RECEPTOR ANTIBODIES

(71) Applicant: The Wistar Institute, Philadelphia, PA (US)

(72) Inventors: Alfredo Perales-Puchalt, Philadelphia, PA (US); David B. Weiner, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 942 days.

(21) Appl. No.: 17/267,331

(22) PCT Filed: Aug. 9, 2019

(86) PCT No.: PCT/US2019/045850
§ 371 (c)(1),
(2) Date: Feb. 9, 2021

(87) PCT Pub. No.: WO2020/033797
PCT Pub. Date: Feb. 13, 2020

(65) Prior Publication Data
US 2021/0340263 A1 Nov. 4, 2021

Related U.S. Application Data

(60) Provisional application No. 62/716,673, filed on Aug. 9, 2018.

(51) Int. Cl.
| | |
|---|---|
| *C07K 14/72* | (2006.01) |
| *A61K 39/00* | (2006.01) |
| *A61K 45/06* | (2006.01) |
| *A61K 47/68* | (2017.01) |
| *A61P 35/00* | (2006.01) |
| *C07K 16/28* | (2006.01) |

(52) U.S. Cl.
CPC .............. *C07K 14/72* (2013.01); *A61K 45/06* (2013.01); *A61K 47/6849* (2017.08); *A61P 35/00* (2018.01); *C07K 16/2869* (2013.01); *A61K 2039/505* (2013.01); *A61K 2039/54* (2013.01)

(58) Field of Classification Search
CPC ................ C07K 16/2869; A61K 45/06; A61K 47/6803; A61K 47/6849; A61K 2039/505; A61K 2039/54; A61P 35/00
See application file for complete search history.

(56) References Cited

U.S. PATENT DOCUMENTS

| | | | | |
|---|---|---|---|---|
| 5,595,756 A | * | 1/1997 | Bally .................... | A61K 9/1272 264/4.1 |
| 2014/0193427 A1 | | 7/2014 | Lerner et al. | |
| 2016/0237160 A1 | | 8/2016 | Votsmeier et al. | |

FOREIGN PATENT DOCUMENTS

| | | | | |
|---|---|---|---|---|
| WO | 1993020199 | | 10/1993 | |
| WO | WO-9320199 A1 | * | 10/1993 | .......... C07K 14/723 |
| WO | WO-2014007198 A1 | * | 1/2014 | ......... A61K 39/3955 |
| WO | WO-2014190305 A2 | * | 11/2014 | .......... C07K 14/755 |
| WO | 2016054153 A1 | | 4/2016 | |

OTHER PUBLICATIONS

Sela-Culang et al., The structural basis of antibody-antigen recognition, 2013, Frontiers in Immunology, vol. 4, Article 302, pp. 1-13 (Year: 2013).*
Kussie et al., A Single Engineered Amino Acid Substitution Changes Antibody Fine Specificity, 1994, Journal of Immunology, pp. 146-152 (Year: 1994).*
Rudikoff et al., Single amino acid substitution altering antigen-binding specificity, 1982, PNAS, vol. 79, pp. 1979-1983 (Year: 1982).*
Mak et al., The Immune Response, Chapter 7—Exploiting Antigen-Antibody Interaction, 2006, p. 1 (Year: 2006).*
Shin, Chimeric antibody: Potential applications for drug delivery and immunotherapy, 1991, Biotherapy, vol. 3, pp. 43-53 (Year: 1991).*
Tao et al., FSH enhances the proliferation of ovarian cancer cells by activating transient receptor potential channel C3, 2013, Endocrine-Related Cancer, vol. 20, pp. 415-429 (Year: 2013).*
Hogenesch et al., Challenges in pre-clinical testing of anti-cancer drugs in cell culture and in animal models, 2012, Journal of Control Release, vol. 164, Issue 2, pp. 183-186 (Year: 2012).*
Shirani et al., Therapeutic Advances and Future Prospects in Progressive Forms of Multiple Sclerosis, 2016, Neurotherapeutics, vol. 13, pp. 58-69 (Year: 2016).*
Mackay et al., Autoimmune Diseases, 2001, The New England Journal of Medicine, vol. 345, No. 5, pp. 340-350 (Year: 2001).*
Radu et al., Expression of Follicle-Stimulating Hormone Receptor in Tumor Blood Vessels, 2010, The New England Journal of Medicine, vol. 363, pp. 1621-1630 (Year: 2010).*
Cleveland Clinic, Bacillus Calmette-Guerin (BCG) Treatment, Cleveland Clinic, 2025, pp. 1-12 (Year: 2025).*
International Search Report and Written Opinion, PCT/US2019/045850, dated Dec. 23, 2019.
Radu, et al., "Expression of Follicule Stimulating Hormone Receptor in Tumor Blood Vessels", N Engl J Med, 363(17):1621-1630 (Oct. 2010).

* cited by examiner

*Primary Examiner* — Jeffrey Stucker
*Assistant Examiner* — Brittney E Donoghue
(74) *Attorney, Agent, or Firm* — Saul Ewing LLP; Kathryn Doyle; Alireza Behrooz

(57) ABSTRACT

The present invention relates to an isolated antibody or antigen binding fragment thereof that bind specifically to the Follicle Stimulating Hormone Receptor (FSHR). Also provided are methods for treating a disease in a subject comprising administering to the subject an isolated antibody or antibody fragment thereof that binds FSHR.

14 Claims, 16 Drawing Sheets
Specification includes a Sequence Listing.

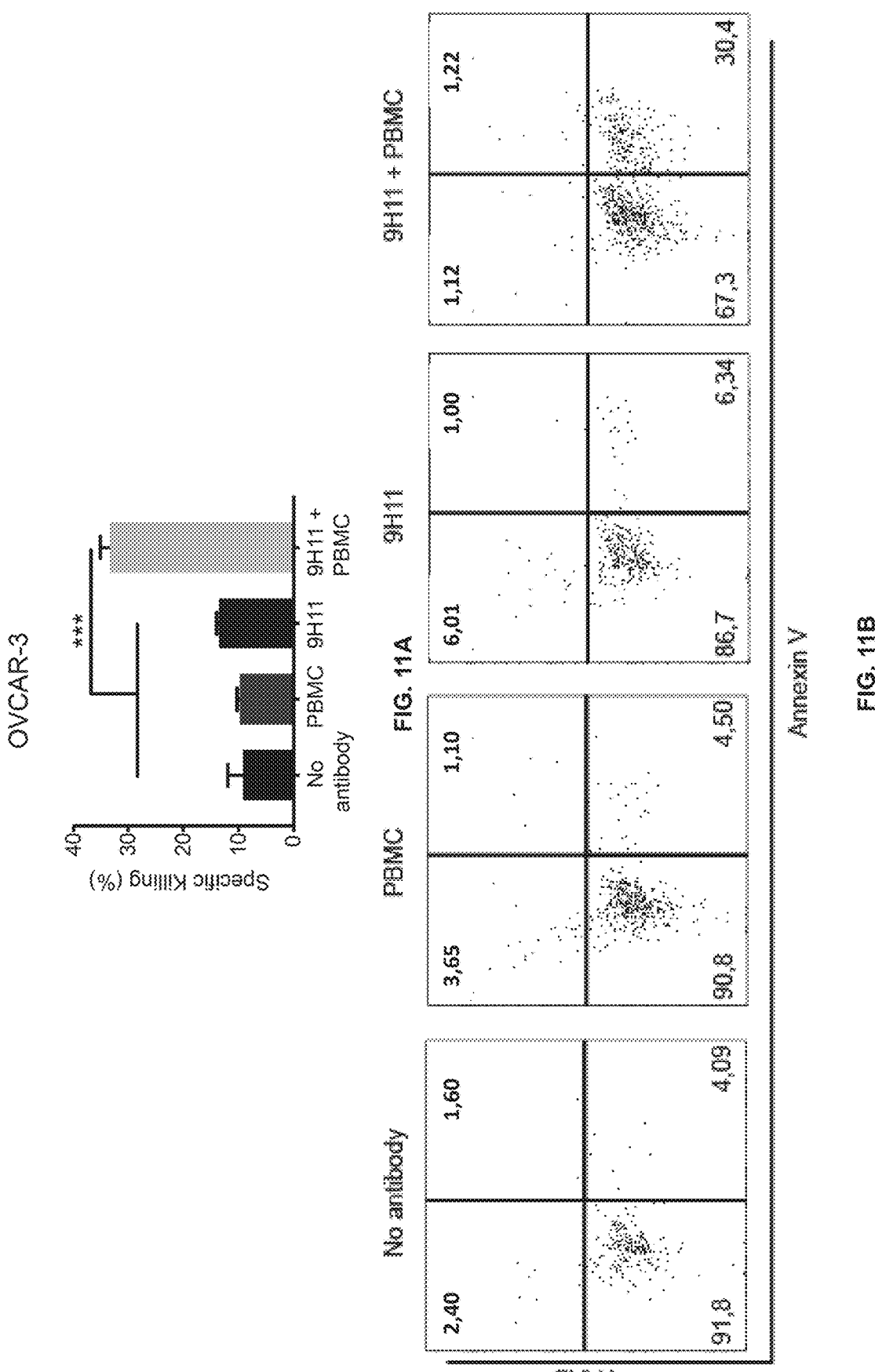

ANTI-FOLLICLE STIMULATING HORMONE RECEPTOR ANTIBODIES

CROSS-REFERENCE TO RELATED APPLICATION

The present application is a 35 U.S.C. § 371 national phase application from, and claiming priority to, International Application No. PCT/US2019/045850, filed Aug. 9, 2019, which claims priority under 35 U.S.C. § 119(e) to U.S. Provisional Patent Application No. 62/716,673, filed Aug. 9, 2018, all of which are hereby incorporated by reference in their entireties.

BACKGROUND OF THE INVENTION

There is a need in the art for antibodies against follicle stimulating hormone receptor (FSHR), for methods of making antibodies against follicle stimulating hormone receptor and methods of their use.

SUMMARY OF THE INVENTION

Provided is an isolated antibody or antigen binding fragment thereof that binds Follicle Stimulating Hormone Receptor (FSHR), wherein the isolated antibody or antigen binding fragment thereof comprises:

A. a heavy chain comprising at least one CDR selected from:
(i) a heavy chain CDR1 having at least 85%, 91%, 92%, 93%, 94%, 95%, 96%, 97%, 98%, 99% or 100% sequence identity to SEQ ID NO: 6;
(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or
(iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;
and/or
B. a light chain comprising at least one CDR selected from:
(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;
(ii) a light chain CDR2 having at least 85%, 91%, 92%, 93%, 94%, 95%, 96%, 97%, 98%, 99% or 100% sequence identity to SEQ ID NO: 3; and/or
(iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments, the isolated antibody or antigen binding fragment thereof comprises a heavy chain CDR1 comprising SEQ ID NO: 6, a heavy chain CDR2 comprising SEQ ID NO: 7, and a heavy chain CDR3 comprising SEQ ID NO: 8, and wherein the antibody or antigen binding fragment thereof comprises a light chain CDR1 comprising SEQ ID NO: 2, a light chain CDR2 comprising SEQ ID NO: 3, and a light chain CDR3 comprising SEQ ID NO: 4.

In some embodiments, the isolated antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 5 and a light chain having at least 91%, 92%, 93%, 94%, 95%, 96%, 97%, 98%, 99% or 100% sequence identity to at least a 10 amino acid consecutive sequence of SEQ ID NO: 1.

In some embodiments, the isolated antibody or antigen binding fragment thereof comprises a heavy chain comprising SEQ ID NO: 5 and a light chain comprising SEQ ID NO: 1.

In some embodiments, the isolated antibody or antigen binding fragment thereof is humanized.

In some embodiments, the isolated antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 10 and a light chain having at least 91%, 92%, 93%, 94%, 95%, 96%, 97%, 98%, 99% or 100% sequence identity to at least a 10 amino acid consecutive sequence of SEQ ID NO: 9.

In some embodiments, the isolated antibody or antigen binding fragment thereof comprises a heavy chain comprising SEQ ID NO: 10 and a light chain comprising SEQ ID NO: 9.

In some embodiments, the isolated antibody or antigen binding fragment thereof is chimeric.

In some embodiments, the isolated antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 13 and a light chain having at least 91%, 92%, 93%, 94%, 95%, 96%, 97%, 98%, 99% or 100% sequence identity to at least a 10 amino acid consecutive sequence of SEQ ID NO: 12.

In some embodiments, the isolated antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 13 and a light chain having at least 91%, 92%, 93%, 94%, 95%, 96%, 97%, 98%, 99% or 100% sequence identity to at least a 10 amino acid consecutive sequence of SEQ ID NO: 9.

In some embodiments, the isolated chimeric antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 10 and a light chain having at least 91%, 92%, 93%, 94%, 95%, 96%, 97%, 98%, 99% or 100% sequence identity to at least a 10 amino acid consecutive sequence of SEQ ID NO: 12.

Also provided is a recombinant nucleic acid encoding the antibody or antigen binding fragment thereof of any one of the preceding aspects or embodiments.

Also provided is an antibody-drug conjugate comprising the antibody or antigen binding fragment of any one of the preceding aspects or embodiments. In some embodiments, the drug is MMAE, ozogamicin, emtansine, amanitin, pyrrolobenzodiazepine (PBD) dimer toxin, a chalichaemicin, a cytotoxic maytansinoid, DM1, carboplatin, cisplatin, paclitaxel, vedotin, or diphtheria toxin.

Also provided is a pharmaceutical composition comprising the isolated antibody or antigen binding fragment of any one of the preceding aspects or embodiments, or the antibody-drug conjugate of any one of the preceding aspects or embodiments.

Provided is a method of treating a disease in a subject in need thereof, comprising administering to the subject an effective amount of the pharmaceutical composition of any one of the preceding aspects or embodiments. In some embodiments, the antibody or antigen binding fragment is administered intravenously, intra-articularly, intraperitoneally, intrathecally, intraventricularly, intrasternally, intracranially, intra-muscularly, subcutaneously, orally or intranasally.

In some embodiments, the method of treating a disease in a subject in need thereof further comprises administering a second agent to the subject. In further embodiments, the second agent is at least one of carboplatin, cisplatin, paclitaxel, docetaxel, gemcitabine, bevacizumab, olaparib, rucaparib, niraparib, cyclophosphamide, FU, abiraterone, flutamide, bicalutamide, leuprolide, goserelin, buserelin, triptorelin, degarelix, Enzalutamide, Apalutamide, Sipuleucel-T, Cabazitaxel, Radium-223, trastuzumab, pertuzumab, lapatinib, tamoxifen, oxaliplatin, capecitabine, leucovorin, Irinotecan, Cetuximab, panitumumab, aflibercept, Regorafenib, Trifluridine-tipiracil, immune checkpoint inhibitors (nivolumab, pembrolizumab), cabozantinib, sunitinib, pazopanib, axitinib, interleukin-2, interferon alpha, mitomycin C, epirubicin, BCG, bleomycin, etoposide, sorafenib, regorafenib, lenvatinib, pemetrexed and/or vinorelbine.

In some embodiments, the disease is cancer. In further embodiments, the cancer is ovarian, prostate, breast, colon, pancreas, urinary bladder, kidney, lung, liver, stomach or testis cancer. In yet further embodiments, the cancer is metastatic.

In some embodiments, the disease is infertility or endometriosis.

Provided is a method of contraception, comprising administering to a subject an effective amount of the pharmaceutical composition of any one of the preceding aspects or embodiments.

In some embodiments, the antibody or antigen binding fragment is administered intravenously, intra-articularly, intraperitoneally, intrathecally, intraventricularly, intrasternally, intracranially, intra-muscularly, subcutaneously, orally or intranasally. In further embodiments, the method of contraception further comprises administering a second agent to the subject. In yet further embodiments, the second agent is at least one of progesterone, estrogen or testosterone.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A shows the structure of the generated FSHR. FIG. 2B shows the depiction of FSHR cloning into pVax1 expression vector. FIG. 2C shows the immunization scheme and bleeding before mice were sacrificed to generate the hybridomas.

FIG. 3A shows the generation of a cell line (K562-hFSHR) by transfecting FSHR gene with a GFP reporter to perform the screening.

FIG. 3B shows that unlike parental cell line K562, K562-hFSHR expresses FSHR by western blot and GFP analyzed by flow cytometry.

FIG. 4A shows cAMP response to different doses of FSH hormone of K562 and K562-hFSHR. FIG. 4B shows a western blot of phospho-Phospho-p44/42 (Erk1/2) and p44/42 (Erk1/2) 20 minutes after stimulation of K562 and K562-FSHR cells using 1 µg/ml FSH.

FIG. 5 shows the potential responses by flow cytometry to the screening of antibodies. If the antibodies analyzed do not bind to the cell lines, both cells (identified by their GFP level) remain in the low x axis. If the antibodies bind non-specifically, both cell lines will appear in the high x axis. If the antibody binds specifically to FSHR, only K562-hFSHR cells will be high on the x axis but K562 cells will be low on the x axis.

FIG. 10A shows the absorbance values of isotype ELISA performed on 9H11 antibody assessing the different immunoglobin isotypes. FIG. 10B shows a picture representing the antibody dependent cellular cytotoxicity mechanism.

FIGS. 11A-11B illustrate that 9H11 mediates ADCC. FIG. 11A shows a histogram of a flow cytometric ADCC assay with K562 and K562-FSHR. FIG. 11B shows flow cytometry plots of a flow cytometric ADCC assay with K562 and K562-FSHR.

FIG. 16 illustrates that 9H11 binds to FSHR by IFA. Immunofluorescence images of 293T cells transfected with

Figure 1:
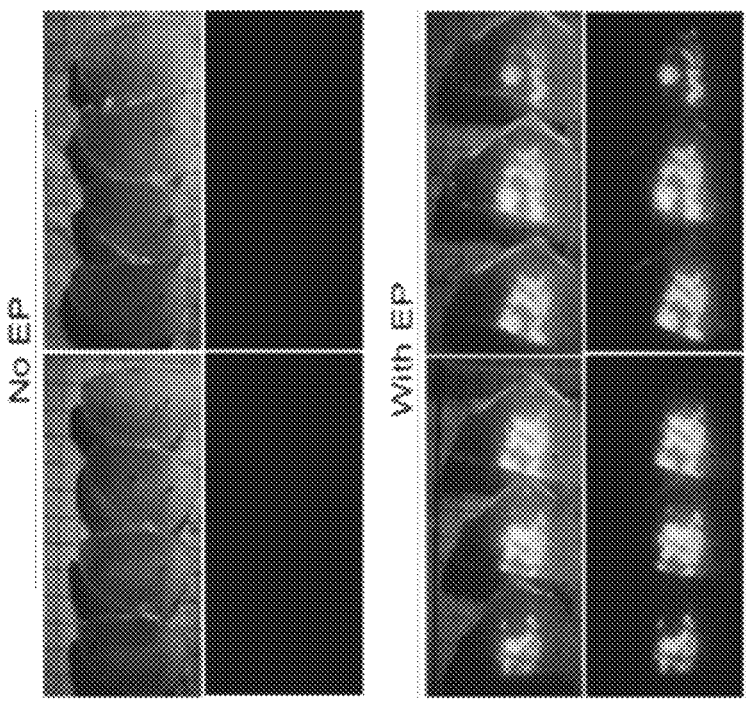
FIG. 1 illustrates that electroporation enhances uptake of DNA encoding human Green Fluorescent Protein (GFP) in muscle cells. Top panel: no electroporation (EP). Bottom panel: with electroporation (EP). Further optimizations include RNA/codon optimization and the use of an effective leader sequence.

5 human FSHR and stained with either mouse anti-human FSHR or 9H11 antibodies followed by secondary anti-mouse IgG are shown. Immunofluorescence images of 293T cells transfected with human FSHR and stained with either mouse anti-mouse FSHR or 9H11 antibodies followed by secondary anti-mouse IgG are also shown. Immunofluorescence images of 293T cells transfected with pVax empty vector and stained with 9H11 antibodies followed by secondary anti-mouse IgG are also shown.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material produced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucle-otides, which can be hydrolyzed into the monomeric "nucleotides." The monomeric nucleotides can be hydro-lyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligo-peptides, homodimers, heterodimers, variants of polypep-tides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expres-sion of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "*Sendai* virus" refers to a genus of the Paramyxoviridae family. *Sendai* viruses are negative, single stranded RNA viruses that do not integrate into the host genome or alter the genetic information of the host cell. *Sendai* viruses have an exceptionally broad host range and are not pathogenic to humans. Used as a recombinant viral vector, *Sendai* viruses are capable of transient but strong gene expression.

A "signal transduction pathway" refers to the biochemical relationship between a variety of signal transduction mol-ecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recog-nizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unla-beled A), in a reaction containing labeled "A" and the antibody, will reduce the amount of labeled A bound to the antibody.

The term "subject" is intended to include living organisms in which an immune response can be elicited (e.g., mam-mals). A "subject" or "patient," as used therein, may be a human or non-human mammal. Non-human mammals include, for example, livestock and pets, such as ovine, bovine, porcine, canine, feline and murine mammals. Pref-erably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substan-tially purified cells refers to a homogenous population of cells. In other instances, this term refers simply to cell that have been separated from the cells with which they are naturally associated in their natural state. In some embodi-ments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, *Sendai* viral vectors, adenoviral vectors, adeno-associated virus vectors, retroviral vectors, lentiviral vectors, and the like.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Antibodies

Provided is an isolated antibody or antigen binding fragment thereof that bind specifically to the Follicle Stimulating Hormone Receptor (FSHR).

In some embodiments, the antibody or antigen binding fragment thereof binds to FSHR. In some embodiments, the FSHR has the amino acid sequence of SEQ ID NO: 11.

MGRLTSSFLLLIVPAYVLSCHHRICHCSNRVFLCQESKVTEIPSDLPRNAI

ELRFVLTKLRVIQKGAFSGFGDLEKIEISQNDVLEVIEADVFSNLPKLHEI

RIEKANNLLYINPEAFQNLPNLQYLLISNTGIKHLPDVHKIHSLQKVLLDI

QDNINIHTIERNSFVGLSFESVILWLNKNGIQEIHNCAFNGTQLDELNLSD

-continued

NNNLEELPNDVFHGASGPVILDISRTISHSLPSYGLENLKKLRARSTYNLK

KLPTLEKLVALMEASLTYPSHCCAFANWRRQISELHPICNKSILRQEVDYM

TQARGQRSSLAEDNESSYSRGFDMTYTEFDYDLCNEVVDVTCSPKPDAFNP

CEDIMGYNILRVLIWFISILAITGNIIVLVILTTSQYKLTVPRFLMCNLAF

ADLCIGIYLLLIASVDIHTKSQYHNYAIDWQTGAGCDAAGFFTVFASELSV

YTLTAITLERWHTITHAMQLDCKVQLRHAASVMVMGWIFAFAAALFPIFGI

SSYMKVSICLPMDIDSPLSQLYVMSLLVLNVLAFVVICGCYIHIYLTVRNP

NIVSSSSDTRIAKRMAMLIFTDFLCMAPISFFAISASLKVPLITVSKAKIL

LVLFHPINSCANPFLYAIFTKNFRRDFFILLSKCGCYEMQAQIYRTETSST

VHNTHPRNGHCSSAPRVTNGSTYILVPLSHLAQN

In some embodiments, the antibody binds to a FSHR having at least 90% sequence identity to at least a 10 amino acid consecutive sequence of SEQ ID NO: 11. In some embodiments, the antibody binds to a FSHR having at least 91%, 92%, 93%, 94%, 95%, 96%, 97%, 98%, 99% or 100% sequence identity to at least a 10 amino acid consecutive sequence of SEQ ID NO: 11. In some embodiments, the antibody is a monoclonal antibody. In some embodiments, the antibody is a chimeric or a humanized antibody.

Also provided is an isolated antibody or antigen binding fragment thereof that binds Follicle Stimulating Hormone Receptor (FSHR), wherein the isolated antibody or antigen binding fragment thereof comprises:

A. a heavy chain comprising at least one CDR selected from:

(i) a heavy chain CDR1 having at least 85%, 91%, 92%, 93%, 94%, 95%, 96%, 97%, 98%, 99% or 100% sequence identity to SEQ ID NO: 6;

(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or (iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;

and/or

B. a light chain comprising at least one CDR selected from:

(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;

(ii) a light chain CDR2 having at least 85%, 91%, 92%, 93%, 94%, 95%, 96%, 97%, 98%, 99% or 100% sequence identity to SEQ ID NO: 3; and/or (iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments, the antibody or antigen binding fragment thereof that binds to FSHR has a heavy chain CDR1 comprising SEQ ID NO: 6, a heavy chain CDR2 comprising SEQ ID NO: 7, and a heavy chain CDR3 comprising SEQ ID NO: 8. In further embodiments, the antibody or antigen binding fragment thereof that binds to FSHR has a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8. In some embodiments, the antibody that binds to FSHR has a light chain CDR1 comprising SEQ ID NO: 2, a light chain CDR2 comprising SEQ ID NO: 3, and a light chain CDR3 comprising SEQ ID NO: 4. In further embodiments, the antibody or antigen binding fragment thereof that binds to FSHR has a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

The murine, humanized and chimeric heavy and light chains described herein may comprise a signal peptide or not. In some embodiments, the antibody or antigen binding fragment thereof that binds FSHR comprises a signal peptide comprising an IgE leader sequence. In some embodiments, the antibody or antigen binding fragment thereof that binds FSHR comprises a signal peptide disclosed herein. In some embodiments, the signal peptide comprises amino acid numbers 1-20 of SEQ ID NO: 14. In some embodiments, the signal peptide comprises amino acid numbers 1-19 of SEQ ID NO: 15. In some embodiments, the signal peptide comprises amino acid numbers 1-18 of SEQ ID NO: 17. In some embodiments, the signal peptide comprises amino acid numbers 1-18 of SEQ ID NO: 16.

In some embodiments, the antibody or antigen binding fragment thereof that binds FSHR has a heavy chain comprising SEQ ID NO: 5 or 15. In further embodiments, the antibody or antigen binding fragment thereof that binds FSHR has a heavy chain having at least 91%, 92%, 93%, 94%, 95%, 96%, 97%, 98%, 99% or 100% sequence identity to at least a 10 amino acid consecutive sequence of SEQ ID NO: 5 or 15. In some embodiments, the antibody that binds FSHR has a light chain comprising SEQ ID NO: 1 or 14. In further embodiments, the antibody or antigen binding fragment thereof that binds FSHR has a light chain having at least 91%, 92%, 93%, 94%, 95%, 96%, 97%, 98%, 99% or 100% sequence identity to at least a 10 amino acid consecutive sequence of SEQ ID NO: 1 or 14.

In some embodiments, the antibody or antigen binding fragment thereof that binds FSHR has a heavy chain comprising SEQ ID NO: 5 or 15 and a light chain comprising SEQ ID NO: 1 or 14. In some embodiments, the antibody or antigen binding fragment thereof that binds FSHR has a heavy chain comprising SEQ ID NO: 5 and a light chain comprising SEQ ID NO: 1 In further embodiments, the antibody or antigen binding fragment thereof that binds FSHR has a heavy chain that consists of SEQ ID NO: 5 and a light chain that consists of SEQ ID NO: 1. This antibody is referred to herein as the 9H11 monoclonal antibody. In further embodiments, the antibody or antigen binding fragment thereof that binds FSHR has a heavy chain having at least 91%, 92%, 93%, 94%, 95%, 96%, 97%, 98%, 99% or 100% sequence identity to at least a 10 amino acid consecutive sequence of SEQ ID NO: 5 or 15 and a light chain having at least 91%, 92%, 93%, 94%, 95%, 96%, 97%, 98%, 99% or 100% sequence identity to at least a 10 amino acid consecutive sequence of SEQ ID NO: 1 or 14.

```
Peptide Sequences

9H11 Murine (original):
Light chain with signal peptide:
Light Signal-VL-CL (kappa)

(SEQ ID NO: 14)
MEKDTLLLWVLLLWVPGSTGDIVLTQSPASLAVSLGQRATISCRASESVDNYGISFLNWFQQ

KPGQPPKLLLYAASNQRSGVPARFSGSGSGTDFSLNIHPMEEDDTAMYFCQQSKEVPWTFGG

GTKVEIKRADAAPTVSIFPPSSEQLTSGGASVVCFLNNFYPKDINVKWKIDGSERQNGVLNS

WTDQDSKDSIYSMSSTLTLTKDEYERHNSYTCEATHKTSTSPIVKSFNRNEC

Light chain without signal peptide:
VL-CL (kappa)

(SEQ ID NO: 1)
DIVLTQSPASLAVSLGQRATISCRASESVDNYGISFLNWFQQKPGQPPKLLIYAASNQRSGV

PARFSGSGSGTDFSLNIHPMEEDDTAMYFCQQSKEVPWTFGGGTKVEIKRADAAPTVSIFPP

SSEQLTSGGASVVCFLNNFYPKDINVKWKTDGSERQNGVLNSWTDQDSKDSIYSMSSTLTLT

KDEYERHNSYTCEATHKTSTSPIVKSFNRNEC

Light chain CDRs:

Light chain CDR1:
                                                          (SEQ ID NO: 2)
RASESVDNYGISFLN Light chain CDR2:
                                                          (SEQ ID NO: 3)
AASNQRS
```

-continued

Light Chain CDR3:

(SEQ ID NO: 4)

QQSKEVPWT

Heavy chain with signal peptide:
Heavy Signal-VH-CH1-Hinge Region-CH2-*CH3*

(SEQ ID NO: 15)

MGRLTSSFLLLIVPAYVLSQVNLKESGPGILQPSQTLNLTCSFSGFSLSTSGMGVGWIRQPS

GKGLDWLAHIWWDDDKRYNPALKSRLTISKDASSNQVFLKIASVVTADTATYYCVQINYGNY

RFDNWGHGTTLTVSSAKTTAPSVYPLAPVCGDTTGSSVTLGCLVKGYFPEPVTLTWNSGSLS

SGVHTFPAVLQSDLYTLSSSVTVTSSTWPSQSITCNVAHPASSTKVDKKIEPRGPTIKPCPP

CKCPAPNLLGGPSVFIFPPPKIKDVLMISLSPIVTCVVVDVSEDDPDVQISWFVNNVEVHTAQ

TQTHREDYNSTLRVVSALPIQHQDWMSGKEFKCKVNNKDLPAPIERTISKPK*GSVRAPQVYV*

*LPPPEEEMTKKQVTLTCMVTDFMPEDIYVEWTNNGKTELNYKNTEPVLDSDGSYFMYSKLRV*

*EKKNWVERNSYSCSVVHEGLHNHHTTKSFSRTPGK*

Heavy chain without signal peptide:
VH-CH1-Hinge Region-CH2-*CH3*

(SEQ ID NO: 5)

QVNLKESGPGILQPSQTLNLTCSFSGFSLSTSGMGVGWIRQPSGKGLDWLAHIWWDDDKRYN

PALKSRLTISKDASSNQVFLKIASVVTADTATYYCVQINYGNYRFDNWGHGTTLTVSSAKTT

APSVYPLAPVCGDTTGSSVTLGCLVKGYFPEPVTLTWNSGSLSSGVHTFPAVLQSDLYTLSS

SVTVTSSTWPSQSITCNVAHPASSTKVDKKIEPRGPTIKPCPPCKCPAPNLLGGPSVFIFPP

KIKDVLMISLSPIVTCVVVDVSEDDPDVQISWFVNNVEVHTAQTQTHREDYNSTLRVVSALP

IQHQDWMSGKEFKCKVNNKDLPAPIERTISKPK*GSVRAPQVYVLPPPEEEMTKKQVTLTCMV*

*TDFMPEDTYVEWTNNGKTELNYKNTEPVLDSDGSYFMYSKLRVEKKNWVERNSYSCSVVHEG*

*LHNHHTTKSFSRTPGK*

Heavy chain CDRs:

Heavy chain CDR1:

(SEQ ID NO: 6)

TSGMGVG

Heavy chain CDR2:

(SEQ ID NO: 7)

HIWWDDDKRYNPALKS

Heavy Chain CDR3:

(SEQ ID NO: 8)

INYGNYRFDN

Also provided is an isolated antibody or antigen binding fragment thereof that cross-competes with an antibody or antigen binding fragment that binds Follicle Stimulating Hormone Receptor (FSHR), wherein the isolated antibody or antigen binding fragment thereof comprises:

A. a heavy chain comprising at least one CDR selected from:
(i) a heavy chain CDR1 having at least 85%, 91%, 92%, 93%, 94%, 95%, 96%, 97%, 98%, 99% or 100% sequence identity to SEQ ID NO: 6;
(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or
(iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;
and/or
B. a light chain comprising at least one CDR selected from:
(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;
(ii) a light chain CDR2 having at least 85%, 91%, 92%, 93%, 94%, 95%, 96%, 97%, 98%, 99% or 100% sequence identity to SEQ ID NO: 3; and/or
(iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an antibody or antigen binding fragment thereof that cross-competes for binding to FSHR with an anti-FSHR antibody comprising a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the antibody or antigen binding fragment thereof that cross-competes for binding to FSHR with an anti-FSHR antibody comprising a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an antibody or antigen binding fragment thereof that cross-competes for binding to FSHR with an anti-FSHR antibody comprising a heavy chain comprising SEQ ID NO: 5 or 15 and a light chain comprising SEQ ID NO: 1 or 14. In further embodiments, the antibody or antigen binding fragment thereof that cross-competes for binding to FSHR with an anti-EMIR antibody has a heavy chain having at least 91%, 92%, 93%, 94%, 95%, 96%, 97%, 98%, 99% or 100% sequence identity to at least a 10 amino acid consecutive sequence of SEQ ID NO: 5 or 15 and a light chain having at least 91%, 92%, 93%, 94%, 95%, 96%, 97%, 98%, 99% or 100% sequence identity to at least a 10 amino acid consecutive sequence of SEQ ID NO: 1 or 14.

In some embodiments, the antibody or antigen binding fragment thereof is an agonist antibody of FSHR. In some embodiments, the antibody or antigen binding fragment thereof blocks interaction between FSHR and FSH. An agonistic antibody may activate antigen presenting cells and promote T-cell responses and foster cytotoxic myeloid cells with the potential to modulate immune response in the absence of T-cell immunity.

In some embodiments, the antibody or antigen binding fragment thereof modulates, blocks, inhibits, reduces, antagonizes, neutralizes or otherwise interferes with the functional activity of FSHR. Such antibodies or antigen binding fragments thereof are referred to herein as "neutralizing anti-FSHR antibodies" or "blocking anti-FSHR antibodies." Functional activities of FSHR include, by way of non-limiting example, interaction with FSH. For example, the anti-FSHR antibodies completely or partially inhibit FSH activity by partially or completely modulating, blocking, inhibiting, reducing, antagonizing, neutralizing, or otherwise interfering with the binding of FSHR to FSH. The anti-FSHR antibodies are considered to completely modulate, block, inhibit, reduce, antagonize, neutralize, or otherwise interfere with FSHR functional activity when the level of FSHR functional activity in the presence of the anti-FSHR antibody is decreased by at least 95%, e.g., by 96%, 97%, 98%, 99%, or 100% as compared to the level of FSHR functional activity in the absence of binding with an anti-FSHR antibody or binding fragment thereof described herein. The anti-FSHR antibodies are considered to partially modulate, block, inhibit, reduce, antagonize, neutralize or otherwise interfere with FSHR functional activity when the level of FSHR activity in the presence of the anti-FSHR antibody is decreased by less than 95%, e.g., by less than 10%, 20%, 25%, 30%, 40%, 50%, 60%, 75%, 80%, 85%, or 90% as compared to the level of FSHR activity in the absence of binding with an anti-FSHR antibody or antigen binding fragment thereof described herein.

In some embodiments, the neutralizing anti-FSHR antibody or antigen binding fragment thereof comprises a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the neutralizing anti-FSHR antibody or antigen binding fragment thereof comprises a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments the neutralizing anti-FSHR antibody or antigen binding fragment thereof comprises a heavy chain comprising SEQ ID NO: 5 or 15 and a light chain comprising SEQ ID NO: 1 or 14. In further embodiments, the neutralizing anti-FSHR antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 5 or 15 and a light chain having at least 91%, 92%, 93%, 94%, 95%, 96%, 97%, 98%, 99% or 100% sequence identity to at least a 10 amino acid consecutive sequence of SEQ ID NO: 1 or 14.

In some embodiments, the neutralizing anti-FSHR antibody or antigen binding fragment thereof comprises an antibody or antigen binding fragment thereof that cross-competes for binding to human FSHR with an anti-FSHR antibody comprising a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the neutralizing anti-FSHR antibody or antigen binding fragment thereof comprises an antibody or antigen binding fragment thereof that cross-competes for binding to human FSHR with an anti-FSHR antibody comprising a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments, the neutralizing anti-FSHR antibody or antigen binding fragment thereof comprises an antibody or antigen binding fragment thereof that cross-competes for binding to human FSHR with an anti-FSHR antibody comprising a heavy chain comprising SEQ ID NO: 5 or 15 and a light chain comprising SEQ ID NO: 1 or 14. In further embodiments, the neutralizing anti-FSHR antibody or antigen binding fragment thereof comprises an antibody or antigen binding fragment thereof that cross-competes for binding to human FSHR with an anti-FSHR antibody comprising a heavy chain having at least 91%, 92%, 93%, 94%, 95%, 96%, 97%, 98%, 99% or 100% sequence identity to at least a 10 amino acid consecutive sequence of SEQ ID NO: 5 or 15 and a light chain having at least 91%, 92%, 93%, 94%, 95%, 96%, 97%, 98%, 99% or 100% sequence identity to at least a 10 amino acid consecutive sequence of SEQ ID NO: 1 or 14.

Single Chain Antibodies

Provided is an isolated single chain antibody that binds specifically to FSHR.

In some embodiments, a single chain antibody specific for binding to FSHR, referred to herein as an "anti-FSHR single chain antibody," is fused to an Fc polypeptide. In some embodiments, the Fc polypeptide is an Fc region of an IgG immunoglobulin, such as an IgG immunoglobulin selected from the group consisting of IgG1 isotype, IgG2 isotype, IgG3 isotype, IgG4 isotype and IgM isotype.

In some embodiments, the anti-FSHR single chain antibody is fused to the carboxy terminus of the Fc polypeptide. In some embodiments, the anti-FSHR single chain antibody is fused to the amino terminus of the Fc polypeptide. The fusions are constructed as a single genetic construct and are expressed in cells in culture.

In some embodiments, the anti-FSHR single chain antibody binds to a FSHR having at least 90% sequence identity to at least a 10 amino acid consecutive sequence of SEQ ID NO: 11. In some embodiments, the antibody binds to a FSHR having at least 91%, 92%, 93%, 94%, 95%, 96%, 97%, 98%, 99% or 100% sequence identity to at least a 10 amino acid consecutive sequence of SEQ ID NO: 11.

In some embodiments, the anti-FSHR single chain antibody comprises a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the anti-FSHR single chain antibody comprises a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an isolated single chain antibody or antigen binding fragment thereof that binds Follicle Stimulating Hormone Receptor (FSHR), wherein the isolated single chain antibody or antigen binding fragment thereof comprises:

A. at least one CDR selected from:
(i) a heavy chain CDR1 having at least 85%, 91%, 92%, 93%, 94%, 95%, 96%, 97%, 98%, 99% or 100% sequence identity to SEQ ID NO: 6;
(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or
(iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;
and/or
B. at least one CDR selected from:
(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;
(ii) a light chain CDR2 having at least 85%, 91%, 92%, 93%, 94%, 95%, 96%, 97%, 98%, 99% or 100% sequence identity to SEQ ID NO: 3; and/or
(iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments the anti-FSHR single chain antibody comprises a heavy chain comprising SEQ ID NO: 5 or 15 and a light chain comprising SEQ ID NO: 1 or 14. In further embodiments, the anti-FSHR single chain antibody comprises a heavy chain having at least 91%, 92%, 93%, 94%, 95%, 96%, 97%, 98%, 99% or 100% sequence identity to at least a 10 amino acid consecutive sequence of SEQ ID NO: 5 or 15 and a light chain having at least 91%, 92%, 93%, 94%, 95%, 96%, 97%, 98%, 99% or 100% sequence identity to at least a 10 amino acid consecutive sequence of SEQ ID NO: 1 or 14.

Humanized Antibody

Provided is a humanized anti-FSHR antibody.

Humanized forms of non-human (e.g. murine) antibodies are genetically engineered chimeric antibodies or antigen binding fragments thereof having preferably minimal portions derived from non-human antibodies. Humanized antibodies include antibodies in which CDRs of a human antibody (recipient antibody) are replaced by residues from a CDR region of a non-human species (donor antibody) such as mouse, rat or rabbit having the desired functionality. In some embodiments, Fv framework residues of the human antibody are replaced by corresponding non-human residues. Humanized antibodies may also comprise residues that are found neither in the recipient antibody nor in the imported CDR or framework (FR) sequences. In some embodiments, the humanized antibody may comprise substantially all of at least one, typically two, variable domains domains in which all or substantially all of the framework regions correspond to those of a relevant human consensus sequence. Humanized antibodies may also include at least a portion of an antibody constant region, such as an Fc region, typically derived from a human antibody (see, for example, Jones et al., 1986. *Nature* 321:522-525; Riechmann et al., 1988. *Nature* 332:323-329; Presta, 1992, *Curr. Op. Struct. Biol.* 2:593-596).

In order to retain high binding affinity, amino acids in the human acceptor sequence may be replaced by the corresponding amino acids from the donor sequence, for example where: (1) the amino acid is in a CDR; (2) the amino acid is in a human framework region (e.g., the amino acid is immediately adjacent to one of the CDRs). See, U.S. Pat. Nos. 5,530,101 and 5,585,089, incorporated herein by reference, which provide detailed instructions for construction of humanized antibodies.

Although humanized antibodies often incorporate all six CDRs (e.g., as defined by Kabat, but often also including hypervariable loop H1 as defined by Chothia) from a mouse antibody, they can also be made with fewer mouse CDRs and/or less than complete mouse CDR sequence(s) (e.g., a functional fragment of a CDR) (e.g., Pascalis et al. *J. Immunol.* 169:3076, 2002; Vajdos et al., *Journal of Molecular Biology*, 320:415-428, 2002; Iwahashi et al., *Mol. Immunol.* 36:1079-1091, 1999; Tamura et al., *Journal of Immunology*, 164:1432-1441, 2000).

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody. However, using certain methods of humanization, the affinity and/or specificity of binding of the antibody for human CD3 antigen may be increased using methods of "directed evolution," as described by Wu et al., J. Mol. Biol., 294:151 (1999), the contents of which are incorporated herein by reference herein in their entirety. In one embodiment, the antibody is a synthetic antibody, human antibody, a humanized antibody, single chain variable fragment, single domain antibody, an antigen binding fragment thereof, and any combination thereof. Provided is a humanized antibody including a light chain comprising at least one CDR from 9H11 and a human variable region framework; and a heavy chain comprising at least one CDR from 9H11 and a human variable region framework. In some embodiments, the humanized antibody includes said light chain and said heavy chain together with a light chain constant region and a heavy chain constant region.

Provided is a humanized antibody or antigen binding fragment thereof that binds Follicle Stimulating Hormone Receptor (FSHR), wherein the antibody or antigen binding fragment thereof comprises a heavy chain CDR1 comprising SEQ ID NO: 6, a heavy chain CDR2 comprising SEQ ID NO: 7, and a heavy chain CDR3 comprising SEQ ID NO: 8, and wherein the antibody or antigen binding fragment thereof comprises a light chain CDR1 comprising SEQ ID NO: 2, a light chain CDR2 comprising SEQ ID NO: 3, and a light chain CDR3 comprising SEQ ID NO: 4. In some embodiments, the humanized antibody comprises fully human framework sequences outside of the CDR regions. In further embodiments, the humanized antibody or antigen binding fragment thereof that binds FSHR comprises a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an isolated humanized antibody or antigen binding fragment thereof that binds Follicle Stimulating Hormone Receptor (FSHR), wherein the isolated antibody or antigen binding fragment thereof comprises:

A. a heavy chain comprising at least one CDR selected from:

(i) a heavy chain CDR1 having at least 85%, 91%, 92%, 93%, 94%, 95%, 96%, 97%, 98%, 99% or 100% sequence identity to SEQ ID NO: 6;

(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or (iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;

and/or

B. a light chain comprising at least one CDR selected from:

(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;

(ii) a light chain CDR2 having at least 85%, 91%, 92%, 93%, 94%, 95%, 96%, 97%, 98%, 99% or 100% sequence identity to SEQ ID NO: 3; and/or (iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Provided is a humanized antibody or antigen binding fragment thereof that binds FSHR, wherein the antibody or antigen binding fragment thereof comprises a light chain comprising SEQ ID NO: 9 or 16 or a heavy chain comprising SEQ ID NO: 10 or 17. In some embodiments, the antibody or antigen binding fragment thereof comprises a light chain comprising SEQ ID NO: 9 or 16 and a heavy chain comprising SEQ ID NO: 10 or 17. In further embodiments, the humanized antibody or antigen binding fragment thereof that binds FSHR has a heavy chain that consists of SEQ ID NO: 10 and a light chain that consists of SEQ ID NO: 9. In further embodiments, the humanized antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 10 or 17 and a light chain having at least 91%, 92%, 93%, 94%, 95%, 96%, 97%, 98%, 99% or 100% sequence identity to at least a 10 amino acid consecutive sequence of SEQ ID NO: 9 or 16.

```
9H11 humanized:
Light chain with signal peptide:
Signal peptide-VL-CL (kappa)

(SEQ ID NO: 16)
MDWTWILFLVAAATRVHSDIQMTQSPSSLSASVGDRVTISCRASESVDNYGISFLNWFQQKP

GKAPKLLIYAASNQRSGVPSRFSGSGSGTDFTLTISSLQPEDFATYFCQQSKEVPWTFGQGT

KVEIKRTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

Light chain without signal peptide:
VL-CL (kappa)

(SEQ ID NO: 9)
DIQMTQSPSSLSASVGDRVTISCRASESVDNYGISFLNWFQQKPGKAPKLLIYAASNQRSGV

PSRFSGSGSGTDFTLTISSLQPEDFATYFCQQSKEVPWTFGQGTKVEIKRTVAAPSVFIFPP

SDEQLKSGTASVVCLLNNFYPREAKVQWKVDNALQSGNSQESVTEQDSKDSTYSLSSTLTLS

KADYEKHKVYACEVTHQGLSSPVTKSFNRGEC

Light chain CDRs:

Light chain CDR1:
                                        (SEQ ID NO: 2)
RASESVDNYGISFLN Light chain CDR2:
                                        (SEQ ID NO: 3)
AASNQRS
```

-continued

Light Chain CDR3:
(SEQ ID NO: 4)
QQSKEVPWT

Heavy chain with signal peptide
Signal peptide-VH-CH1-Hinge Region-CH2-*CH3*
(SEQ ID NO: 17)
MDWTWILFLVAAATRVHS EVQLVESGGGLVQPGGSLRLSCSFSGFSLSTSGMGVGWIRQAPG

KGLEWVAHIWWDDDKRYNPALKSRFTLSVDRSKNTLYLQMNSLRAEDTATYYCVQINYGNYR

FDNWGHGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAK*GQPREPQVYTL*

*PPSRDELTKNQVSLTCLVKGFYPSDIAVEWESNGQPENNYKTTPPVLDSDGSFFLYSKLTVD*

*KSRWQQGNVFSCSVMHEALHNHYTQKSLSLSPGK*

Heavy chain without signal peptide
VH-CH1-Hinge Region-CH2-*CH3*
(SEQ ID NO: 10)
EVQLVESGGGLVQPGGSLRLSCSFSGFSLSTSGMGVGWIRQAPGKGLEWVAHIWWDDDKRYN

PALKSRFTLSVDRSKNTLYLQMNSLRAEDTATYYCVQINYGNYRFDNWGHGTLVTVSSASTK

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAK*GQPREPQVYTLPPSRDELTKNQVSLTCLV*

*KGFYPSDIAVEWESNGQPENNYKTTPPVLDSDGSFFLYSKLTVDKSRWQQGNVFSCSVMHEA*

*LHNHYTQKSLSLSPGK*

Heavy chain CDRs:

Heavy chain CDR1:
(SEQ ID NO: 6)
TSGMGVG

Heavy chain CDR2:
(SEQ ID NO: 7)
HIWWDDDKRYNPALKS

Heavy Chain CDR3:
(SEQ ID NO: 8)
INYGNYRFDN

Also provided is a humanized antibody or antigen binding fragment thereof that cross-competes for binding to FSHR with an anti-FSHR antibody comprising a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the humanized antibody or antigen binding fragment thereof cross-competes for binding to FSHR with an anti-FSHR antibody comprising a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an isolated humanized antibody or antigen binding fragment thereof that cross-competes with a humanized antibody or antigen binding fragment that binds Follicle Stimulating Hormone Receptor (FSHR), wherein the isolated humanized antibody or antigen binding fragment thereof comprises:

A. a heavy chain comprising at least one CDR selected from:

(i) a heavy chain CDR1 having at least 85%, 91%, 92%, 93%, 94%, 95%, 96%, 97%, 98%, 99% or 100% sequence identity to SEQ ID NO: 6;

(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or (iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;

and/or

B. a light chain comprising at least one CDR selected from:

(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;

(ii) a light chain CDR2 having at least 85%, 91%, 92%, 93%, 94%, 95%, 96%, 97%, 98%, 99% or 100% sequence identity to SEQ ID NO: 3; and/or (iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is a humanized antibody or antigen binding fragment thereof that cross-competes for binding to FSHR with an anti-FSHR antibody comprising a heavy chain comprising SEQ ID NO: 10 or 17 and a light chain comprising SEQ ID NO: 9 or 16. In further embodiments, the humanized antibody or antigen binding fragment thereof that cross-competes for binding to FSHR with an anti-FSHR antibody has a heavy chain having at least 91%, 92%, 93%, 94%, 95%, 96%, 97%, 98%, 99% or 100% sequence identity to at least a 10 amino acid consecutive sequence of SEQ ID NO: 10 or 17 and a light chain having at least 91%, 92%, 93%, 94%, 95%, 96%, 97%, 98%, 99% or 100% sequence identity to at least a 10 amino acid consecutive sequence of SEQ ID NO: 9 or 16.

In some embodiments, the humanized antibody or antigen binding fragment thereof is an agonist antibody of FSHR. In some embodiments, the antibody or antigen binding fragment thereof blocks interaction between FSHR and FSH. An agonistic antibody may activate antigen presenting cells and promote T-cell responses and foster cytotoxic myeloid cells with the potential to modulate immune response in the absence of T-cell immunity.

In some embodiments, the humanized antibody or antigen binding fragment thereof modulates, blocks, inhibits, reduces, antagonizes, neutralizes or otherwise interferes with the functional activity of FSHR. Such antibodies or antigen binding fragments thereof are referred to herein as "neutralizing anti-FSHR antibodies" or "blocking anti-FSHR antibodies." Functional activities of FSHR include, by way of non-limiting example, interaction with FSH. For example, the anti-FSHR antibodies completely or partially inhibit FSH activity by partially or completely modulating, blocking, inhibiting, reducing, antagonizing, neutralizing, or otherwise interfering with the binding of FSHR to FSH. The anti-FSHR antibodies are considered to completely modulate, block, inhibit, reduce, antagonize, neutralize, or otherwise interfere with FSHR functional activity when the level of FSHR functional activity in the presence of the anti-FSHR antibody is decreased by at least 95%, e.g., by 96%, 97%, 98%, 99%, or 100% as compared to the level of FSHR functional activity in the absence of binding with an anti- FSHR antibody or binding fragment thereof described herein. The anti-FSHR antibodies are considered to partially modulate, block, inhibit, reduce, antagonize, neutralize or otherwise interfere with FSHR functional activity when the level of FSHR activity in the presence of the anti-FSHR antibody is decreased by less than 95%, e.g., by less than 10%, 20%, 25%, 30%, 40%, 50%, 60%, 75%, 80%, 85%, or 90% as compared to the level of FSHR activity in the absence of binding with an anti-FSHR antibody or antigen binding fragment thereof described herein.

In some embodiments, the humanized neutralizing anti-FSHR antibody or antigen binding fragment thereof comprises a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the humanized neutralizing anti-FSHR antibody or antigen binding fragment thereof comprises a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments the humanized neutralizing anti-FSHR antibody or antigen binding fragment thereof comprises a heavy chain comprising SEQ ID NO: 10 and a light chain comprising SEQ ID NO: 9. In further embodiments, the neutralizing anti-FSHR antibody or antigen binding fragment thereof comprises a heavy chain having at least 91%, 92%, 93%, 94%, 95%, 96%, 97%, 98%, 99% or 100% sequence identity to at least a 10 amino acid consecutive sequence of SEQ ID NO: 10 or 17 and a light chain having at least 91%, 92%, 93%, 94%, 95%, 96%, 97%, 98%, 99% or 100% sequence identity to at least a 10 amino acid consecutive sequence of SEQ ID NO: 9 or 16.

In some embodiments, the humanized neutralizing anti-FSHR antibody or antigen binding fragment thereof comprises an antibody or antigen binding fragment thereof that cross-competes for binding to human FSHR with an anti-FSHR antibody comprising a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the humanized neutralizing anti-FSHR antibody or antigen binding fragment thereof comprises an antibody or antigen binding fragment thereof that cross-competes for binding to human FSHR with an anti-FSHR antibody comprising a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments, the humanized neutralizing anti-FSHR antibody or antigen binding fragment thereof comprises an antibody or antigen binding fragment thereof that cross-competes for binding to human FSHR with an anti-FSHR antibody comprising a heavy chain comprising SEQ ID NO: 10 or 17 and a light chain comprising SEQ ID NO: 9 or 16. In further embodiments, the neutralizing anti-FSHR antibody or antigen binding fragment thereof comprises an antibody or antigen binding fragment thereof that cross-competes for binding to human FSHR with an anti-FSHR antibody comprising a heavy chain having at least 91%, 92%, 93%, 94%, 95%, 96%, 97%, 98%, 99% or 100% sequence identity to at least a 10 amino acid consecutive sequence of SEQ ID NO: 10 or 17 and a light chain having at least 91%, 92%, 93%, 94%, 95%, 96%, 97%, 98%, 99% or 100% sequence identity to at least a 10 amino acid consecutive sequence of SEQ ID NO: 9 or 16.

Humanized Single Chain Antibodies

Provided is an isolated humanized single chain antibody that binds specifically to FSHR.

In some embodiments, a humanized single chain antibody specific for binding to FSHR, referred to herein as a "humanized anti-FSHR single chain antibody," is fused to an Fc polypeptide. In some embodiments, the Fc polypeptide is an Fc region of an IgG immunoglobulin, such as an IgG immunoglobulin selected from the group consisting of IgG1 isotype, IgG2 isotype, IgG3 isotype, IgG4 isotype and IgM isotype.

In some embodiments, the humanized anti-FSHR single chain antibody is fused to the carboxy terminus of the Fc polypeptide. In some embodiments, the humanized anti-FSHR single chain antibody is fused to the amino terminus of the Fc polypeptide. The fusions are constructed as a single genetic construct and are expressed in cells in culture.

In some embodiments, the humanized anti-FSHR single chain antibody binds to a FSHR having at least 90% sequence identity to at least a 10 amino acid consecutive sequence of SEQ ID NO: 11. In some embodiments, the antibody binds to a FSHR having at least 91%, 92%, 93%, 94%, 95%, 96%, 97%, 98%, 99% or 100% sequence identity to at least a 10 amino acid consecutive sequence of SEQ ID NO: 11.

In some embodiments, the humanized anti-FSHR single chain antibody comprises a heavy chain CDR1 comprising SEQ ID NO: 6, a heavy chain CDR2 comprising SEQ ID NO: 7, a heavy chain CDR3 comprising SEQ ID NO: 8, a light chain CDR1 comprising SEQ ID NO: 2, a light chain CDR2 comprising SEQ ID NO: 3, and a light chain CDR3 comprising SEQ ID NO: 4. In further embodiments, the humanized anti-FSHR single chain antibody comprises a heavy chain CDR1 having at least 85%, 91%, 92%, 93%, 94%, 95%, 96%, 97%, 98%, 99% or 100% sequence identity to SEQ ID NO: 6, a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7, and a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8, a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2, a light chain CDR2 having at least 85%, 91%, 92%, 93%, 94%, 95%, 96%, 97%, 98%, 99% or 100% sequence identity to SEQ ID NO: 3, and a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

Also provided is an isolated humanized single chain antibody or antigen binding fragment thereof that binds Follicle Stimulating Hormone Receptor (FSHR), wherein the isolated humanized single chain antibody or antigen binding fragment thereof comprises:

A. at least one CDR selected from:

(i) a heavy chain CDR1 having at least 85%, 91%, 92%, 93%, 94%, 95%, 96%, 97%, 98%, 99% or 100% sequence identity to at least SEQ ID NO: 6;

(ii) a heavy chain CDR2 having at least 85%, 91%, 92%, 93%, 94%, 95%, 96%, 97%, 98%, 99% or 100% sequence identity to at least a 7 amino acid consecutive sequence of SEQ ID NO: 7; and/or (iii) a heavy chain CDR3 having at least 85%, 91%, 92%, 93%, 94%, 95%, 96%, 97%, 98%, 99% or 100% sequence identity to at least a 7 amino acid consecutive sequence of SEQ ID NO: 8;

and/or

B. at least one CDR selected from:

(i) a light chain CDR1 having at least 85%, 91%, 92%, 93%, 94%, 95%, 96%, 97%, 98%, 99% or 100% sequence identity to at least a 7 amino acid consecutive sequence of SEQ ID NO: 2;

(ii) a light chain CDR2 having at least 85%, 91%, 92%, 93%, 94%, 95%, 96%, 97%, 98%, 99% or 100% sequence identity to SEQ ID NO: 3; and/or (iii) a light chain CDR3 having at least 85%, 91%, 92%, 93%, 94%, 95%, 96%, 97%, 98%, 99% or 100% sequence identity to at least a 7 amino acid consecutive sequence of SEQ ID NO: 4.

In some embodiments the humanized anti-FSHR single chain antibody comprises a heavy chain comprising SEQ ID NO: 10 or 17 and a light chain comprising SEQ ID NO: 9 or 16. In further embodiments, the anti-FSHR single chain antibody comprises a heavy chain having at least 91%, 92%, 93%, 94%, 95%, 96%, 97%, 98%, 99% or 100% sequence identity to at least a 10 amino acid consecutive sequence of SEQ ID NO: 10 or 17 and a light chain having at least 91%, 92%, 93%, 94%, 95%, 96%, 97%, 98%, 99% or 100% sequence identity to at least a 10 amino acid consecutive sequence of SEQ ID NO: 9 or 16.

Chimeric Antibodies

Also provided is a chimeric antibody or antigen binding fragment thereof that binds to FSHR. A chimeric antibody is an antibody in which a portion of the variable region of a mouse (or other non-human species) antibody is combined with the constant region of a human antibody. In some embodiments, the entire variable region of the mouse antibody is combined with the constant region of a human antibody.

In some embodiments, the chimeric antibody or antigen binding fragment thereof that binds to FSHR comprises a chimeric light chain comprising SEQ ID NO: 12 and a chimeric heavy chain comprising SEQ ID NO: 13.

Chimeric Light Chain With Signal Peptide:

Signal peptide-VL-CL (kappa)

SEQ ID NO: 18)
MDWTWILFLVAAATRVHSDIQMTQSPASLAVSLGQRATISCRASESVDNYGISFLNWFQQKP

GQPPKLLIYAASNQRSGVPARFSGSGSGTDFSLNIHPMEEDDTAMYFCQQSKEVPWTFGGGT

KVEIKRTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

Chimeric Light Chain Without Signal Peptide:

VL-CL (kappa)

(SEQ ID NO: 12)
DIQMTQSPASLAVSLGQRATISCRASESVDNYGISFLNWFQQKPGQPPKLLIYAASNQRSGV

PARFSGSGSGTDFSLNIHPMEEDDTAMYFCQQSKEVPWTFGGGTKVEIKRTVAAPSVPIFPP

SDEQLKSGTASVVCLLNNFYPREAKVQWKVDNALQSGNSQESVTEQDSKDSTYSLSSTLTLS

KADYEKHKVYACEVTHQGLSSPVTKSFNRGEC

Light chain CDRs:

Light chain CDR1:

(SEQ ID NO: 2)
RASESVDNYGISFLN

Light chain CDR2:

(SEQ 10 NO: 3)
AASNQRS

Light Chain CDR3:

SEQ ID NO: 4)
QQSKEVPWT

Chimeric Heavy Chain With Signal Peptide:

Signal peptide-VH-CH1-Hinge Region-CH2-*CH3*

(SEQ ID NO: 19)
MDWTWILFLVAAATRVHSEVQLKESGPGILQPSQTLNLTCSFSGFSLSTSGMGVGWIRQPSG

KGLDWLAHIWWDDDKRYNPALKSRLTISKDASSNQVFLKIASVVTADTATYYCVQINYGNYR

FDNWGHGTTLTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAK*GQPREPQVYTL*

*PPSRDELTKNQVSLTCLVKGFYPSDIAVEWESNGQPENNYKTTPPVLDSDGSFFLYSKLTVD*

*KSRWQQGNVFSCSVMHEALHNHYTQKSLSLSPGK*

Chimeric Heavy Chain Without Signal Peptide:

VH-CH1-Hinge Region-CH2-CH3

(SEQ ID NO: 13)
EVQLKESGPGILQPSQTLNLTCSFSGFSLSTSGMGVGWIRQPSGKGLDWLAHIWWDDDKRYN

PALKSRLTISKDASSNQVFLKIASVVTADTATYYCVQINYGNYRFDNWGHGTTLTVSSASTK

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVLT

-continued
VLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMHEA

LHNHYTQKSLSLSPGK

Heavy chain CDRs:

Heavy chain CDR1:
                                                        (SEQ ID NO: 6)
TSGMENG Heavy chain CDR2:
                                                        (SEQ ID NO: 7)
HIWWDDDKRYNPALKS Heavy Chain CDR3:
                                                        (SEQ ID NO: 8)
INYGNYRFDN In further embodiments, the chimeric antibody or antigen binding fragment thereof that binds to FSHR comprises a chimeric light chain having at least 91%, 92%, 93%, 94%, 95%, 96%, 97%, 98%, 99% or 100% sequence identity to at least a 10 amino acid consecutive sequence of SEQ ID NO: 12 or 18 and a chimeric heavy chain having at least 91%, 92%, 93%, 94%, 95%, 96%, 97%, 98%, 99% or 100% sequence identity to at least a 10 amino acid consecutive sequence of SEQ ID NO: 13 or 19.

In some embodiments, the chimeric antibody or antigen binding fragment thereof that binds to FSHR comprises a chimeric light chain comprising SEQ ID NO: 12 and a humanized heavy chain comprising SEQ ID NO: 10. In further embodiments, the chimeric antibody or antigen binding fragment thereof that binds to FSHR comprises a chimeric light chain having at least 91%, 92%, 93%, 94%, 95%, 96%, 97%, 98%, 99% or 100% sequence identity to at least a 10 amino acid consecutive sequence of SEQ ID NO: 12 and a humanized heavy chain having at least 91%, 92%, 93%, 94%, 95%, 96%, 97%, 98%, 99% or 100% sequence identity to at least a 10 amino acid consecutive sequence of SEQ ID NO: 10.

In some embodiments, the chimeric antibody or antigen binding fragment thereof that binds to FSHR comprises a humanized light chain comprising SEQ ID NO: 9 and a chimeric heavy chain comprising SEQ ID NO: 13. In further embodiments, the chimeric antibody or antigen binding fragment thereof that binds to FSHR comprises a humanized light chain having at least 91%, 92%, 93%, 94%, 95%, 96%, 97%, 98%, 99% or 100% sequence identity to at least a 10 amino acid consecutive sequence of SEQ ID NO: 9 and a chimeric heavy chain having at least 91%, 92%, 93%, 94%, 95%, 96%, 97%, 98%, 99% or 100% sequence identity to at least a 10 amino acid consecutive sequence of SEQ ID NO: 13.

Molecular Biology Techniques

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Bahar, 2011); "Current Protocols in Immunology" (Coligan, 2002). These techniques are applicable to the production of the polynucleotides and polypeptides of the invention, and, as such, may be considered in making and practicing the invention. The engineered cytokines of the invention were codon optimized so as to enhance their ability to modulate the immune response in a mammal into which they are introduced. The invention includes sequences that are homologous to the sequences disclosed herein. Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts), "Percentage of similarity" is calculated using PAUP* 4.0b10 software (D. L. Swofford, Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

Nucleic Acids

Introduction of a nucleic acid encoding any of the engineered antibodies of the invention into a mammal or introduction of a nucleic acid encoding FSHR into the cells of a mammal for the purpose of generating anti-FSHR antibodies can be accomplished using technology available in the art, disclosed, for example, in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are also incorporated herein by reference.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the antibody or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration. In order to maximize antibody production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells. In some embodiments for which protein is used, i.e., the engineered antibodies of the invention, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well-known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning, Third Ed. Cold Spring Harbor Press (2001) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning Third Ed. Cold Spring Harbor Press (2001). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The polynucleotides encoding the engineered antibodies of the invention may be delivered using any of several well-known technologies including DNA injection (also referred to as DNA vaccination), recombinant vectors such as recombinant adenovirus, recombinant adenovirus associated virus and recombinant vaccinia virus.

Routes of administration include, but are not limited to, intramuscular, intranasal, intraperitoneal, intradermal, subcutaneous, intravenous, intra-arterial, intraocular and oral as well as topical, transdermal, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HCV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 .mu.s, 20

.mu.s, 10 .mu.s or 1 .mu.s, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules.

In some embodiments, the pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

Antibody-Drug Conjugates

Provided are antibody-drug conjugates (ADCs) comprising an antibody or antigen binding fragment thereof that binds FSHR. In some embodiments, the drug is MMAE (monomethyl auristatin E), ozogamicin, emtansine, amanitin, pyrrolobenzodiazepine (PBD) dimer toxin, a chalichaemicin, a cytotoxic maytansinoid, for example DM1.

In some embodiments, the drug is connected to the antibody or antigen binding fragment thereof via a linker. Suitable linkers are known in the art. See for example U.S. Pat. No. 8,742,076, which is hereby incorporated by reference in its entirety.

Pharmaceutical Compositions

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

It will be appreciated by a person skilled in the art that the antibody or antigen binding fragment may be administered in admixture with a suitable pharmaceutical excipient diluent or carrier selected with regard to the intended route of administration and standard pharmaceutical practice. For example, see Remington: The Science and Practice of Pharmacy, 19th edition, 1995, Ed. Alfonso Gennaro, Mack Publishing Company, Pennsylvania, USA.

In some embodiments, the antibody or antigen binding fragment may be administered orally, bucally or sublingually in the form of tablets, capsules, ovules, elixirs, solutions or suspensions, which may contain flavoring or coloring agents, for immediate, delayed or controlled-release applications. The antibody or antigen binding fragment may also be administered via intracavernosal injection.

The antibody or antigen binding fragment may also be administered parenterally. In some embodiments, the antibody or antigen binding fragment may be administered intravenously, intra-articularly, intraperitoneally, intrathecally, intraventricularly, intrasternally, intracranially, intramuscularly or subcutaneously. In some embodiments, the antibody or antigen binding fragment is administered by infusion techniques.

In some embodiments, the antibody or antigen binding fragment is used in the form of a sterile aqueous solution that may contain other substances, for example, sufficient salts or glucose (or other sugars) to make the solution isotonic with blood. The aqueous solution should be suitably buffered (preferably to a pH of from 3 to 9), if necessary. The preparation of suitable parenteral formulations under sterile conditions is readily accomplished by standard pharmaceutical techniques well known to a person of skill in the art.

Formulations suitable for parenteral administration include aqueous and non-aqueous sterile injection solutions which may contain and-oxidants, buffers, bacteriostats and solutes which render the formulation isotonic with blood. Suitable formulations for parenteral administration also include aqueous and non-aqueous suspensions which may include suspending agents and thickening agents. The formulations may be presented in unit-dose or multi-dose containers.

For oral, parenteral or other routes of administration to human patients, the daily dosage level of the antibody or antigen binding fragment that binds FSHR will usually be from 1 to 1000 mg per adult (i.e., from about 0.015 to 15 mg/kg), administered in single or multiple or divided doses.

In some embodiments, the dosage level may be from about 0.5 mg/kg to about 10 mg/kg. In further embodiments, the dosage level may be from about 2 to about 6 mg/kg.

In some embodiments, the antibody or antigen binding fragment is administered intranasally or by inhalation. The antibody or antigen binding fragment may be delivered in the form of a dry powder inhaler or an aerosol spray from a pressurized container, pump, spray or nebulizer with the use of a propellant.

In some embodiments, the antibody or antigen binding fragment is administered by DNA injection and electroporation of the DNA encoded antibody into muscle or skin.

Methods of Treatment

Provided is a method of treating a disease in a subject in need thereof, comprising administering to the subject an effective amount of any one of the antibody or antigen binding fragments described herein. In some embodiments, the subject is human. In some embodiments, the antibody or antigen binding fragment is provided in a pharmaceutical composition.

In some embodiments, the pharmaceutical composition may be delivered orally, parenterally, for example as a parenteral injection, intravenously, for example as an intravenous infusion, or by inhalation.

In some embodiments, a sample is a tissue or a bodily fluid sample. In some embodiments, the sample is a tumor sample, a blood sample, a blood plasma sample, a peritoneal fluid sample, an exudate or an effusion.

In some embodiments, a second agent is administered to the subject. In further embodiments, the second agent is at least one of carboplatin, cisplatin, paclitaxel, docetaxel, gemcitabine, bevacizumab, olaparib, rucaparib, niraparib, cyclophosphamide, FU, abiraterone, flutamide, bicalutamide, leuprolide, goserelin, buserelin, triptorelin, degarelix, Enzalutamide, Apalutamide, Sipuleucel-T, Cabazitaxel, Radium-223, trastuzumab, pertuzumab, lapatinib, tamoxifen, oxaliplatin, capecitabine, leucovorin, Irinotecan, Cetuximab, panitumumab, aflibercept, Regorafenib, Trifluridine-tipiracil, immune checkpoint inhibitors (nivolumab, pembrolizumab), cabozantinib, sunitinib, pazopanib, axitinib, interleukin-2, interferon alpha, mitomycin C, epirubicin, BCG, bleomycin, etoposide, sorafenib, regorafenib, lenvatinib, pemetrexed and/or vinorelbine. In some embodiments, the second agent is an alkylating agent, antimetabolite, antibiotic, a plant-derived agent, platinum complex, campthotecin derivative, tyrosine kinase inhibitor, monoclonal antibody, interferon, biological response modifier, hormonal anti-tumor agent, anti-tumor viral agent, angiogenesis inhibitor, differentiating agent, PI3K/mTOR/AKT inhibitor, cell cycle inhibitor, apoptosis inhibitor, hsp 90 inhibitor, tubulin inhibitor, DNA repair inhibitor, anti-angiogenic agent, receptor tyrosine kinase inhibitor, topoisomerase inhibitor, taxane, agent targeting Her-2, hormone antagonist, agent targeting a growth factor receptor, or a pharmaceutically acceptable salt thereof. In some embodiments, the anti-tumor agent is citabine, capecitabine, valopicitabine or gemcitabine. In some embodiments, the anti-tumor agent is Avastin, Sutent, Nexavar, Recentin, ABT-869, Axitinib, Irinotecan, topotecan, paclitaxel, docetaxel, lapatinib, Herceptin, tamoxifen, progesterone, a steroidal aromatase inhibitor, a non-steroidal aromatase inhibitor, Fulvestrant, an inhibitor of epidermal growth factor receptor (EGFR), Cetuximab, Panitumimab, an inhibitor of insulin-like growth factor 1 receptor (IGF1R), and/or CP-751871.

In some embodiments, the disease is cancer. In further embodiments, the cancer is ovarian, prostate, breast, colon, pancreas, urinary bladder, kidney, lung, liver, stomach and/or testis cancer or metastasis therefrom. FSHR has been found in the blood vessels of said tumors and their metastases (Radu et al., (2010). Expression of follicle-stimulating hormone receptor in tumor blood vessels. *N Engl J Med* 363(17): 1621-1630).

In some embodiments, the ovarian cancer is metastatic ovarian cancer. In further embodiments, the ovarian cancer is deficient in homologous recombination DNA repair. In some embodiments, the ovarian cancer is FSH dependent. In some embodiments, the ovarian cancer is BRCA deficient. In some embodiments, the BRCA-deficiency is in BRCA-1 or BRCA-2. In further embodiments, the BRCA-deficiency is in both BRCA-1 and BRCA-2.

In some embodiments, the prostate cancer is metastatic prostate cancer. In further embodiments, the prostate cancer is deficient in homologous recombination DNA repair.

In some embodiments, the prostate cancer is androgen dependent. In some embodiments, the method optionally results in an increased prostate specific antigen (PSA) index in the subject.

In some embodiments the disease is infertility or endometriosis.

In some embodiments anti-FSHR antibodies or fragments thereof of the invention can be used to induce transient contraception in males or females. In some embodiments, a second agent is administered. In further embodiments, the second agent is at least one of progesterone, estrogen or testosterone.

Antibody-Drug Conjugate (ADC)

In one aspect, the invention includes a method for treating cancer in a subject, the method comprising administering to the subject an effective amount of an antibody-drug conjugate (ADC), wherein the antibody or antigen binding fragment portion of the ADC binds to FSHR. In some embodiments, the drug used to make the ADC is MMAE (monomethyl auristatin E), ozogamicin, emtansine, amantin, pyrrolobenzodiazepine (PBD) dimer toxin, a chalichaemicin, a cytotoxic maytansinoid, for example DM1.

In some embodiments, the drug is connected to the antibody or antigen binding fragment thereof via a linker. Suitable linkers are known in the art. See for example U.S. Pat. No. 8,742,076, which is hereby incorporated by reference in its entirety.

Antibody-Dependent Cell-Mediated Cytotoxicity (ADCC)

Antibody-dependent cell-mediated cytotoxicity (ADCC) is a cell-mediated reaction in which nonspecific cytotoxic cells that express Fc receptors (FcRs), such as natural killer (NK) cells, neutrophils and macrophages, recognize bound antibody on a target cell and subsequently cause lysis of the target cell. The primary cells for mediating ADCC, NK cells, express FcgRIII only, whereas monocytes express FcgRI, FcgRII and FcgRIII. FcR expression on hematopoietic cells is summarized in Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

In some embodiments, administering to the subject an effective amount of any one of the antibody or antigen binding fragments described herein results in ADCC.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Generation of Monoclonal Antibody 9H11

Figures 2A, 2B, 2C:
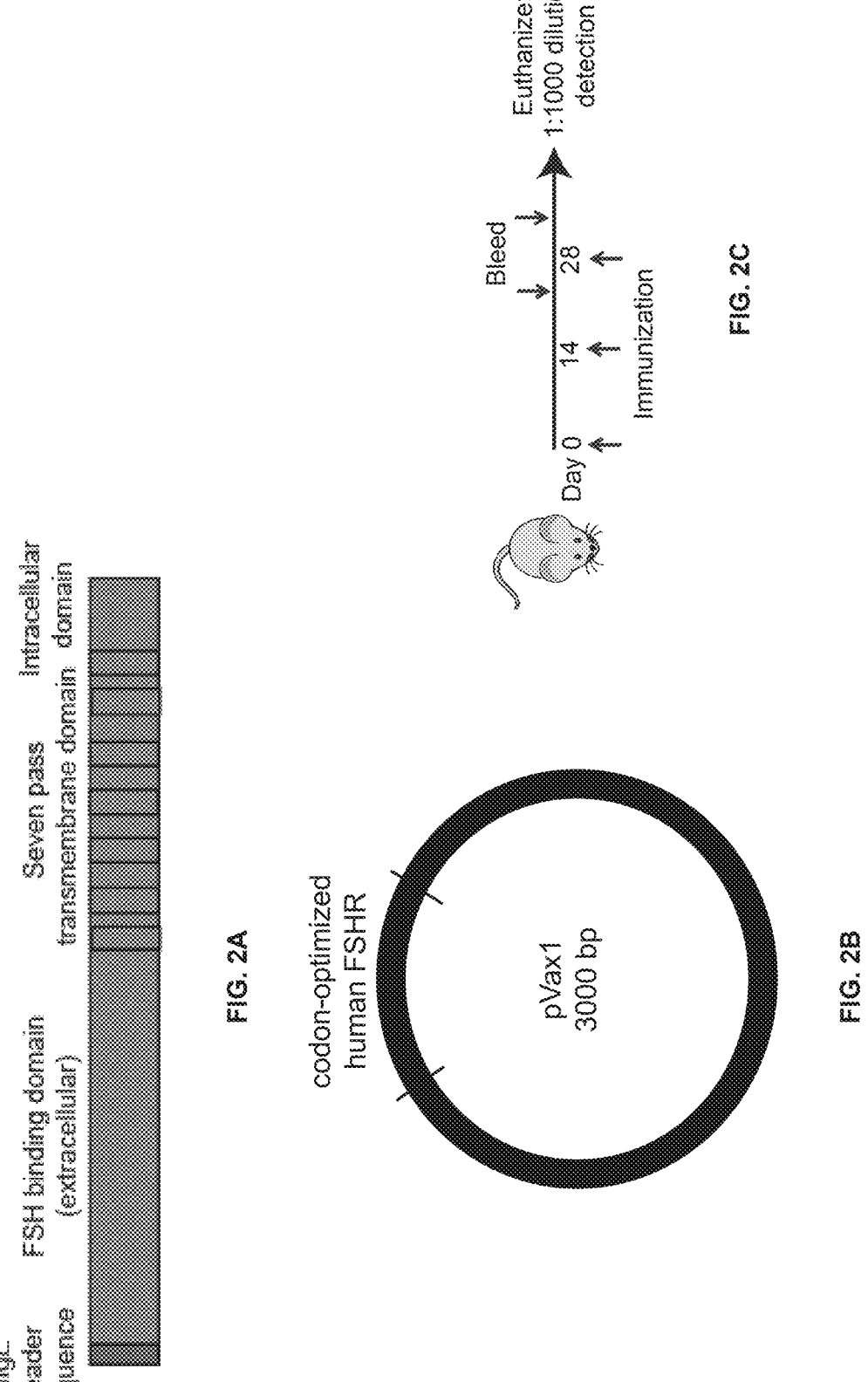
FIGS. 2A-2C illustrate the vaccination strategy.
Figure 3B:
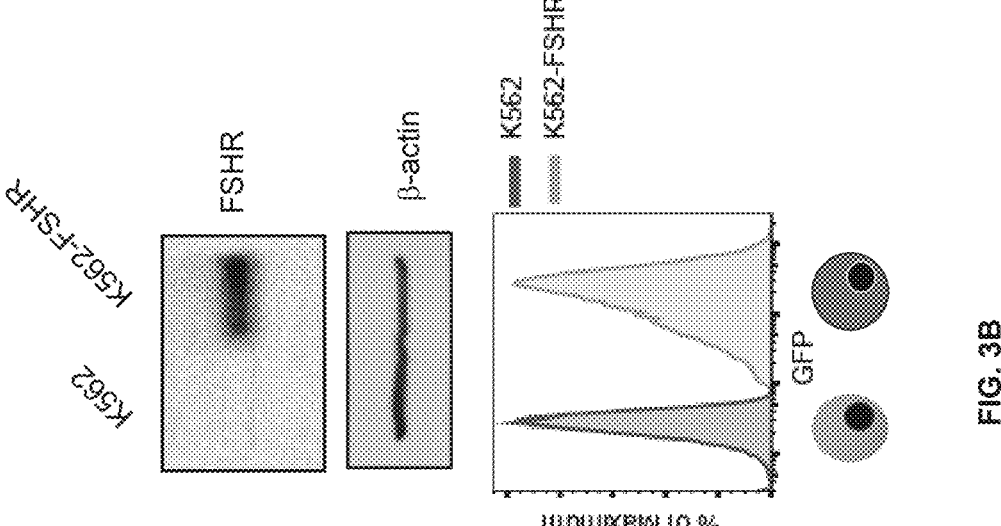
FIGS. 3A-3B illustrate the generation of a screening method for FSHR-binding antibodies.
Figure 3A:
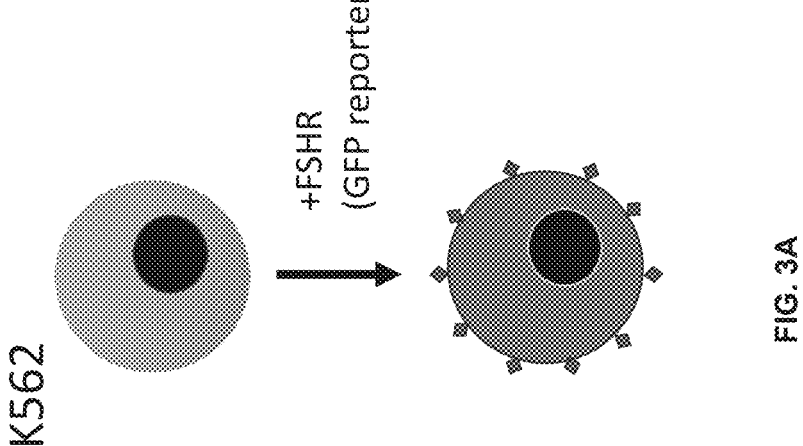
Figure 4B:
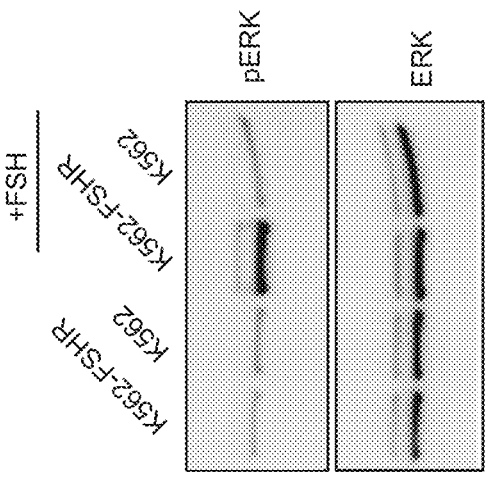
FIGS. 4A-4B illustrate that the FSHR signals properly.
Figure 4A:
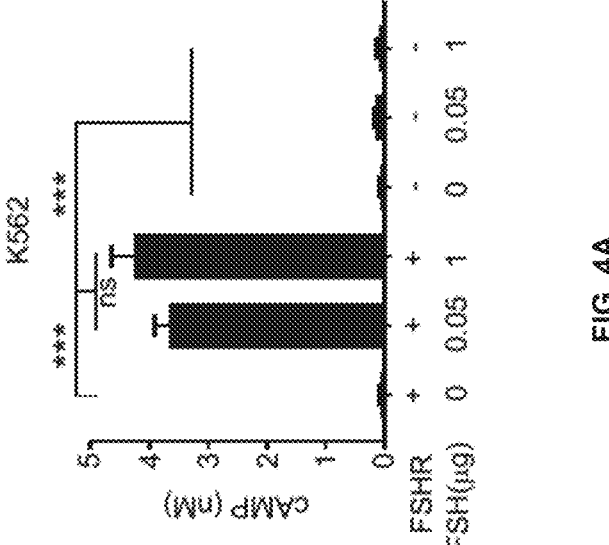
Figure 5:
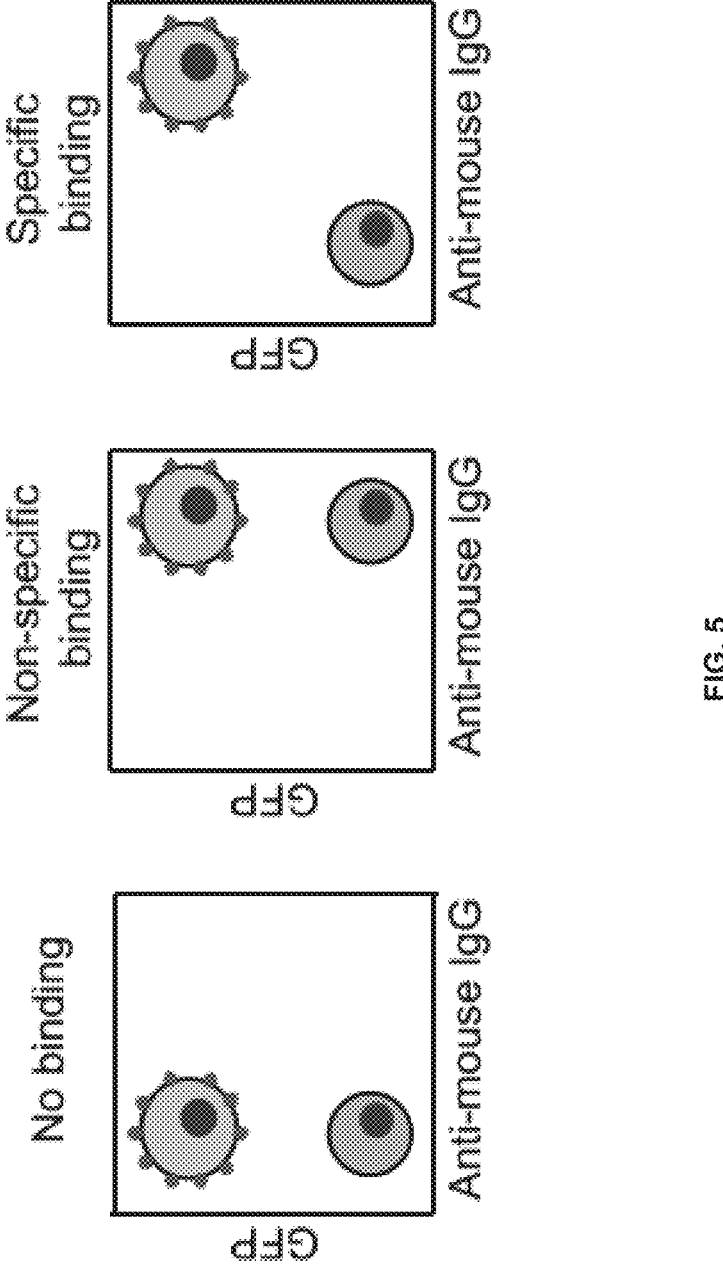
FIG. 5 illustrates the generation of a screening method for FSHR-binding antibodies.
Figure 6:
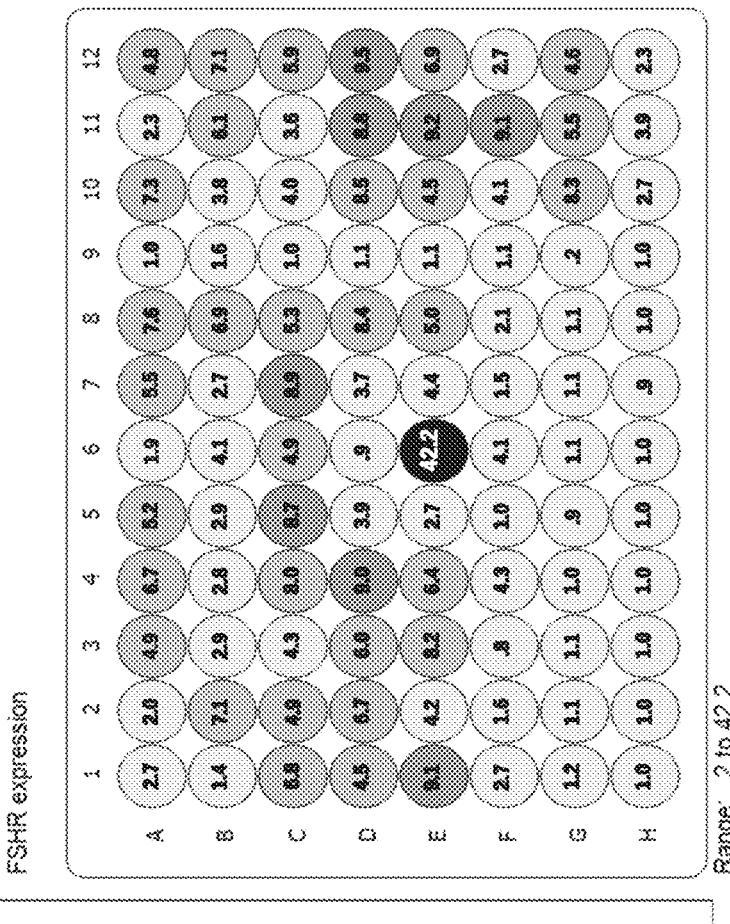
FIG. 6 illustrates the vaccination and screening strategy. The figure is representative of a flow cytometric screening output strategy for detection of FSHR binding antibodies from hybridomas as flow plot and mean fluorescent intensity fold of K562-Fhsr/K562.
Figure 7:
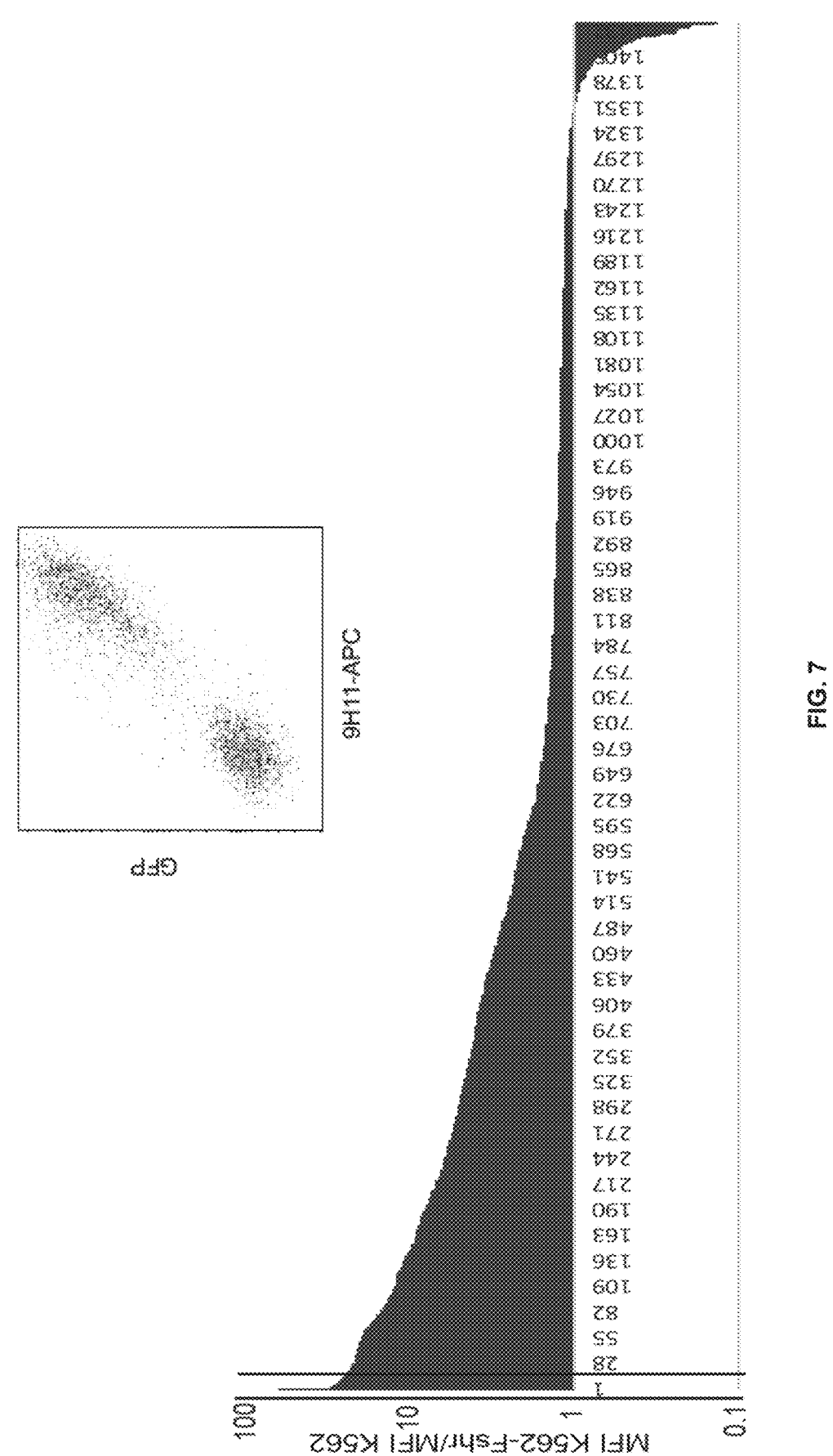
FIG. 7 illustrates that murine monoclonal antibody 9H11 showed the best binding to FSHR. The figure shows a waterfall plot depicting the hybridoma supernatant binding to FSHR measured as MFI K562-Fshr/MFI K562 ratio. The top 20 clones were selected (left of the black vertical bar). A flow cytometry plot of K562 (GFP–)/K562-Fhsr (GFP+) cells stained with 9H11 monoclonal antibody followed by anti-mouse IgG APC is also shown.

To generate monoclonal antibodies against FSHR, Balb/c mice were immunized with an optimized DNA construct encoding human FSHR (FIGS. 2A-2C). The DNA (25 μg) was injected in the tibialis anterior muscle followed by electroporation every 2 weeks (FIG. 2C). A week after DNA injection the mice were bled and anti-FSHR antibodies were checked for using flow cytometry culturing a mix of FSHR positive (+) and negative (−) cells with the mouse sera (FIGS. 3A-5). After obtaining a 20-fold increase of intensity of positive over negative cells at a 1:1000 sera dilution, the mice were boosted with cells overexpressing FSHR and 4 days later the mice were sacrificed and their splenocytes were fused with with Sp2.0/0. The resulting hybridomas were screened for by flow cytometry (FIGS. 6-7) and the 20 hybridomas with highest fold intensity over the negative controls were selected for continued research.

Example 2: Monoclonal Antibody 9H11 Mediates ADCC

To determine its ability to induce ADCC, the FSHR+ cell line OVCAR3 was co-incubated with human PBMC in the presence or absence of 9H11 antibody. It was observed that 9H11 was able to induce ADCC only when the target cells had physiological levels of FSHR (FIGS. 11A-11B).

Example 3: Monoclonal Antibody 9H11 Delays Progression of Ovarian Cancer

Figure 13:
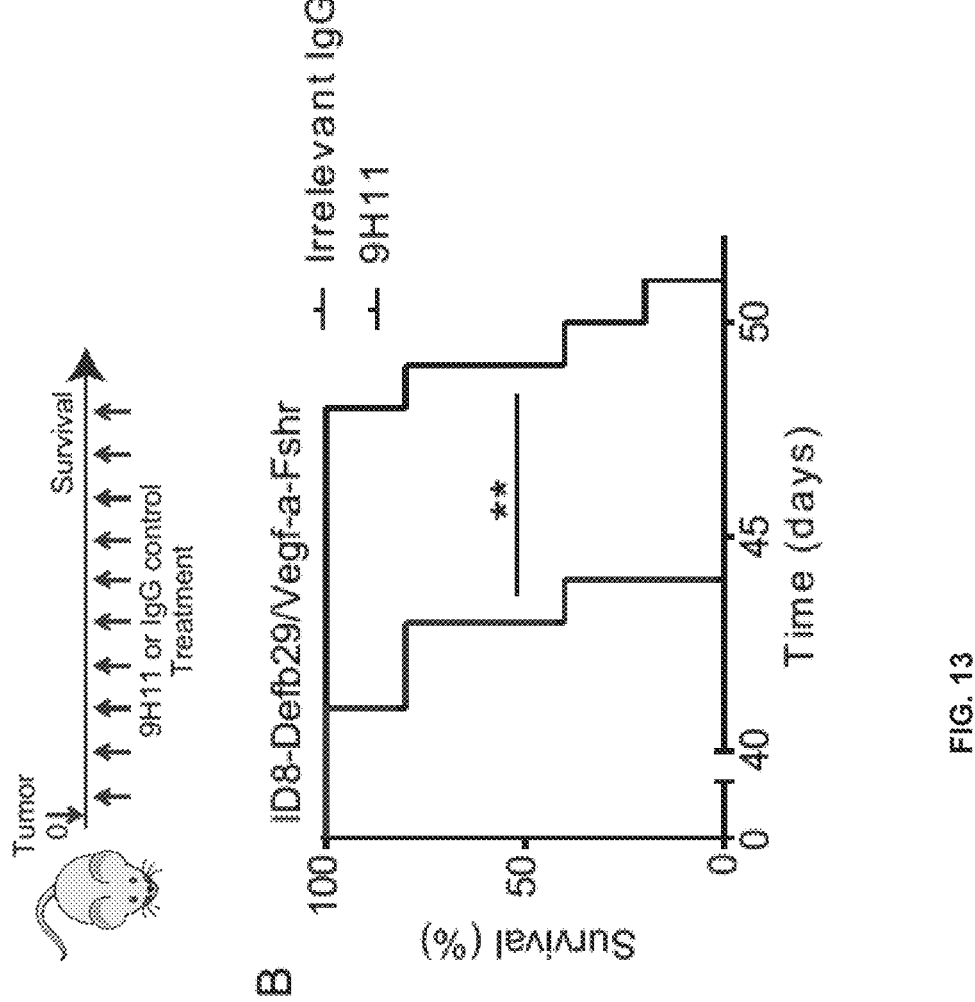
FIG. 13 illustrates that 9H11 delays progression of ovarian cancer. A schematic of tumor challenge experiments and a survival curve of of ID8-Defb29/Vegf-a-Fshr bearing mice treated with 9H11 or polyclonal mouse IgG are shown.

To test if the antibody dependent cellular cytotoxicity elicited by 9H11 translated into an in vivo anti-tumor effect, the ability of 9H11 to bind to murine FSHR was taken advantage of. Mice were challenged with ID8-Defb29/Vegf-a-Fshr and treated with 9H11 or irrelevant antibodies. 9H11 alone was able to delay tumor progression of this highly aggressive model of peritoneally metastatic ovarian cancer (FIG. 13).

Example 4: Generation of the Humanized Antibody

Figure 14:
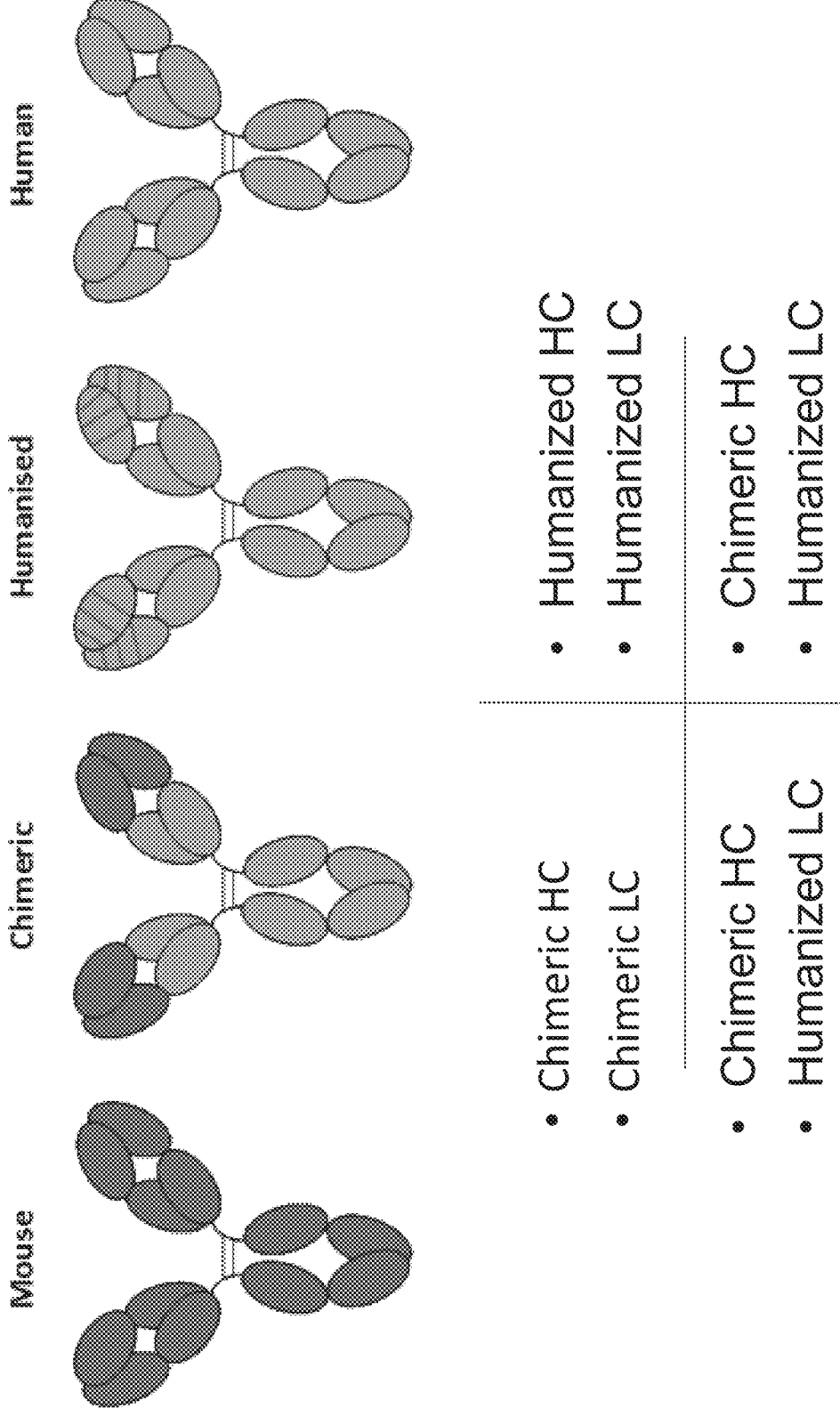
FIG. 14 illustrates the chimerization and humanization of 9H11.
Figure 15:
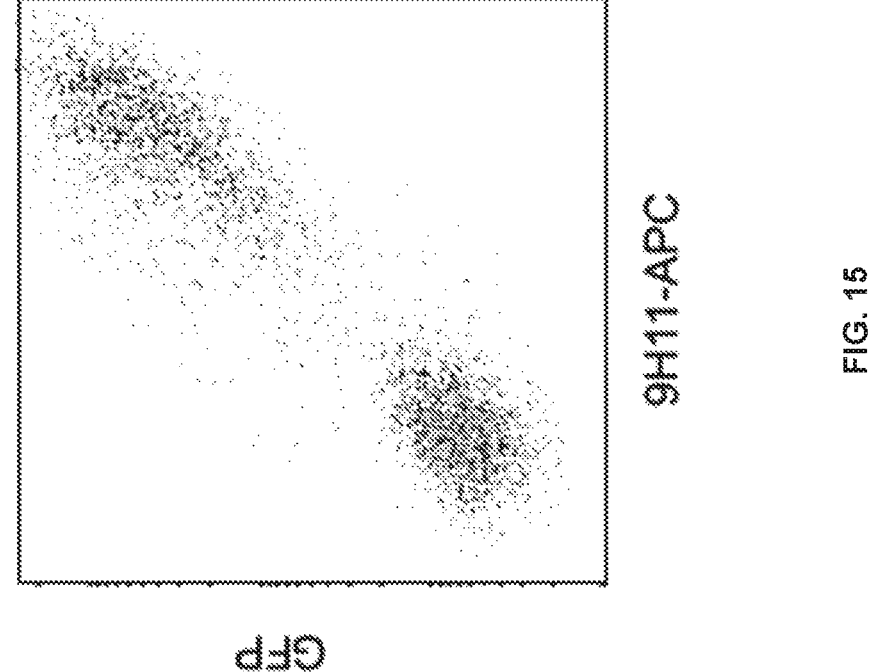
FIG. 15 illustrates that humanized 9H11 (Hu9H11) retains binding to FSHR. A flow cytometry plot of K562 (GFP–)/K562-Fhsr (GFP+) cells stained with humanized 9H11 monoclonal antibody followed by anti-human IgG PE is shown.

To make 9H11 more amenable for use in humans, it was humanized. Versions of its heavy and light chains were generated as both a chimeric (with human constant regions and murine variable regions) or fully humanized (with human constant and variable regions except for the CDRs, which were murine). Antibodies resulting from the combination of all 4 chains were tested and it was found that the fully humanized heavy and light chains paired into an antibody that retained binding to FSHR (FIGS. 14 and 15).

Example 5: 9H11 Binds by Flow Cytometry to Human and Murine FHSR

Figure 8:
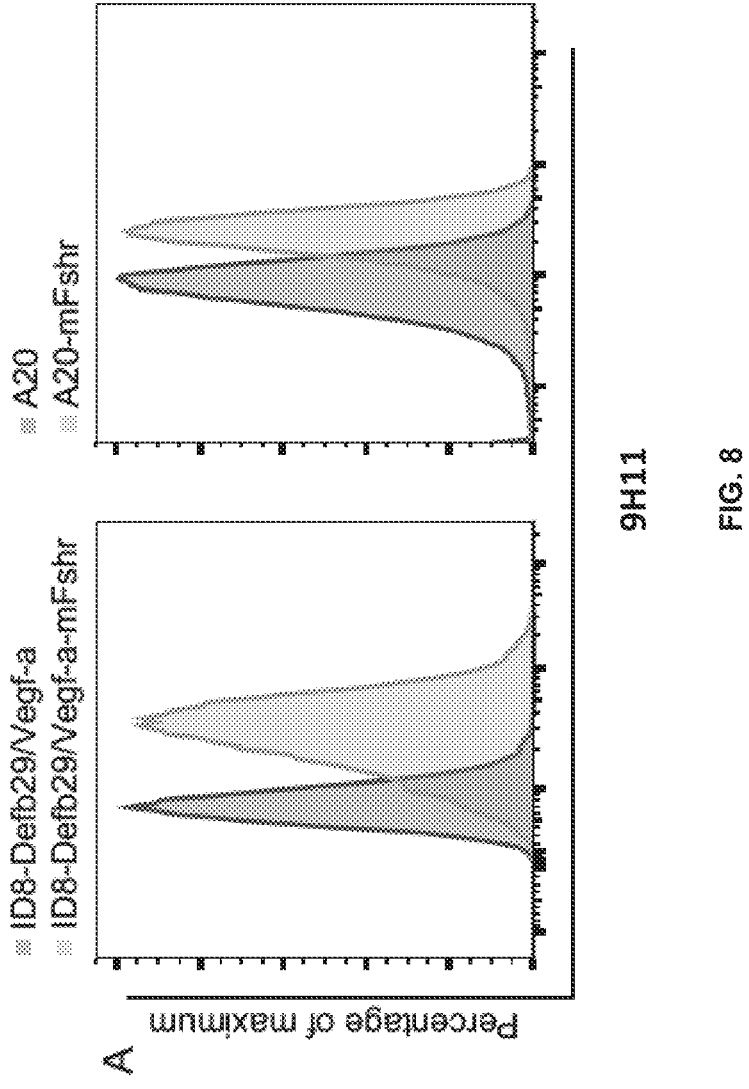
FIG. 8 illustrates that 9H11 also binds murine FSHR. The figure shows a flow cytometry plot of A20(GFP–)/A20-Fhsr (GFP+) and ID8-Defb29/Vegf-a vs. ID8-Defb29/Vegf-a-Fshr cells stained with 9H11 (both cell lines were transfected with murine FSHR).
Figure 9:
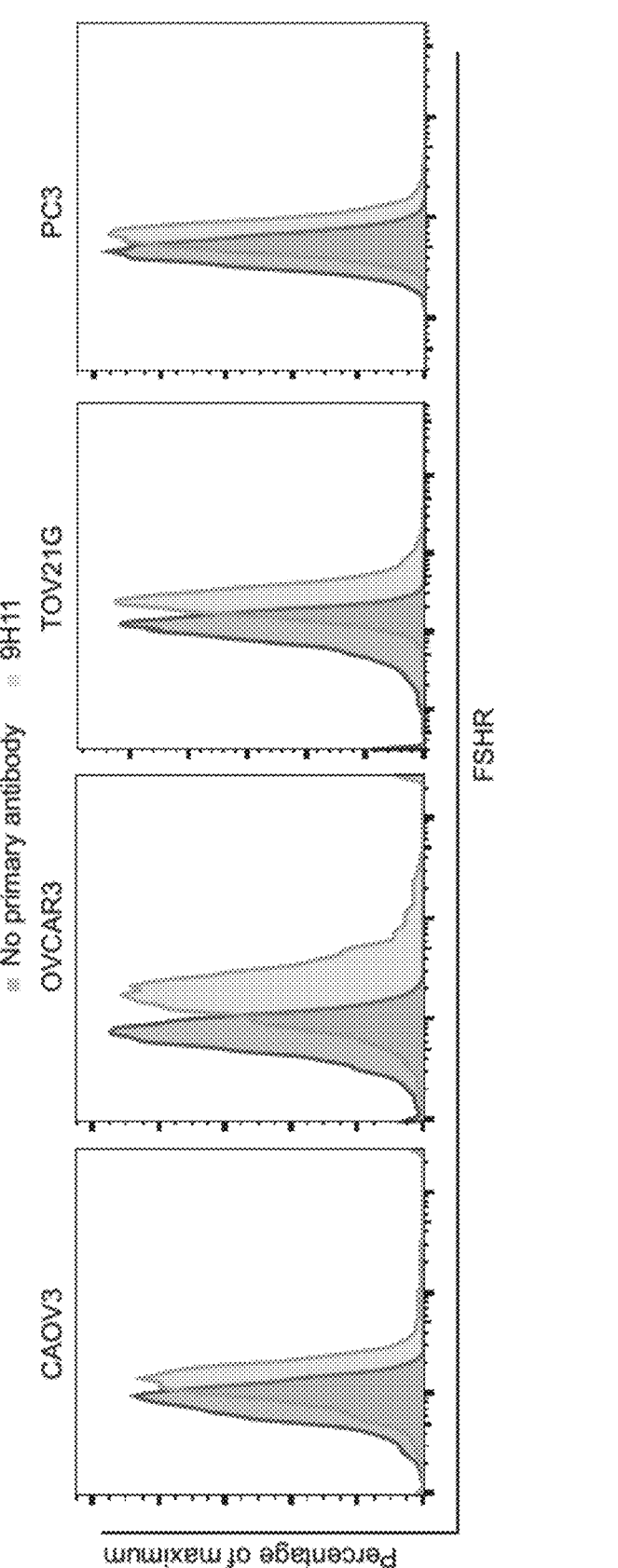
FIG. 9 illustrates that 9H11 binds to human ovarian cancer cell lines with physiological levels of FSHR. Flow cytometry plot of Caov3, OVCAR3, TOV21G and PC3 human cell lines stained with 9H11 (naturally expressing FSHR).
Figures 10A, 10B:
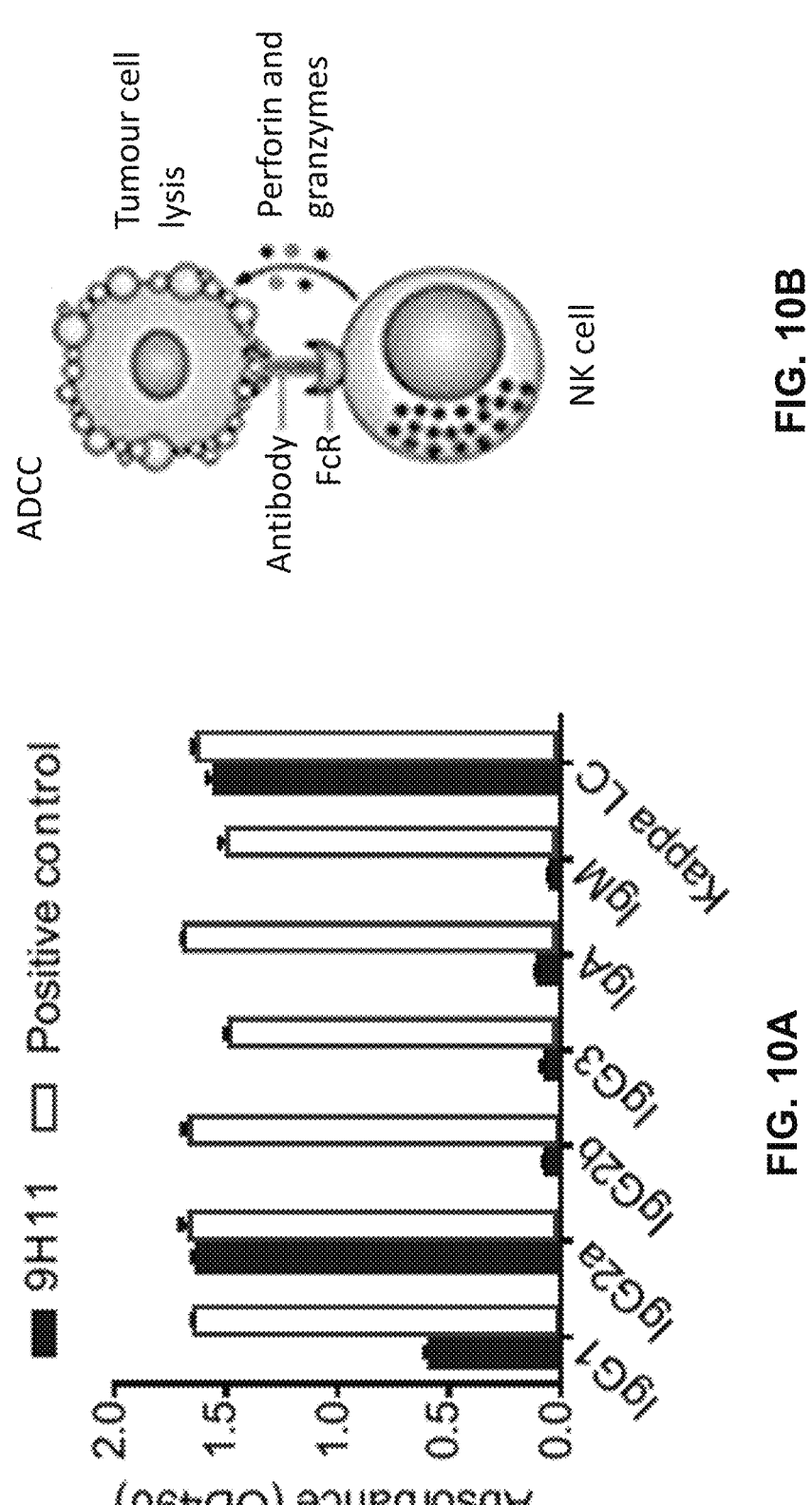
FIGS. 10A-10B illustrate that 9H11 is IgG2a-Kappa.
Figure 12:
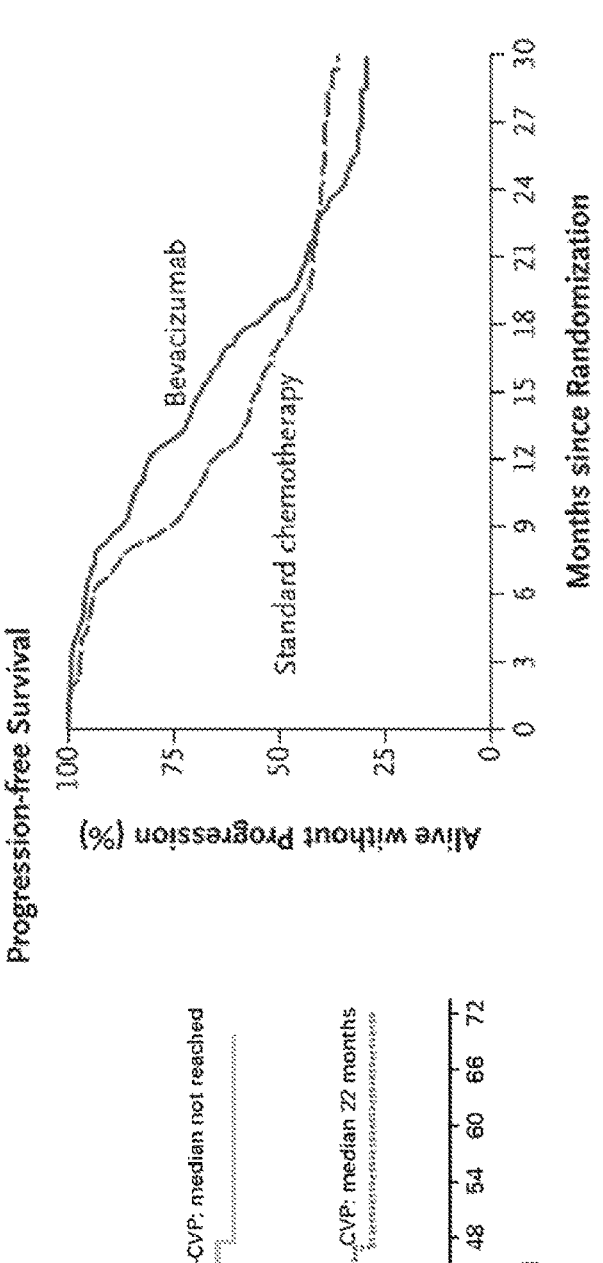
FIG. 12 illustrates whether ADCC is sufficient to obtain a clinical benefit. The graph on the left shows event-free probability, and the graph on the right shows progression-free survival percentages.

The 9H11 antibody was used to bind murine cells that did not express FSHR in its native form before and after expression of murine FSHR. 9H11 was able to bind to murine FSHR by flow cytometry (FIG. 8). Flow cytometry binding to naturally expressing human FSHR cell lines was also tested. Expression of FSHR was detected when CAOV3, OVCAR2, TOV-21G and PC3 cell lines were stained versus when a non-specific antibody was used (FIG. 9).

Figure 16:
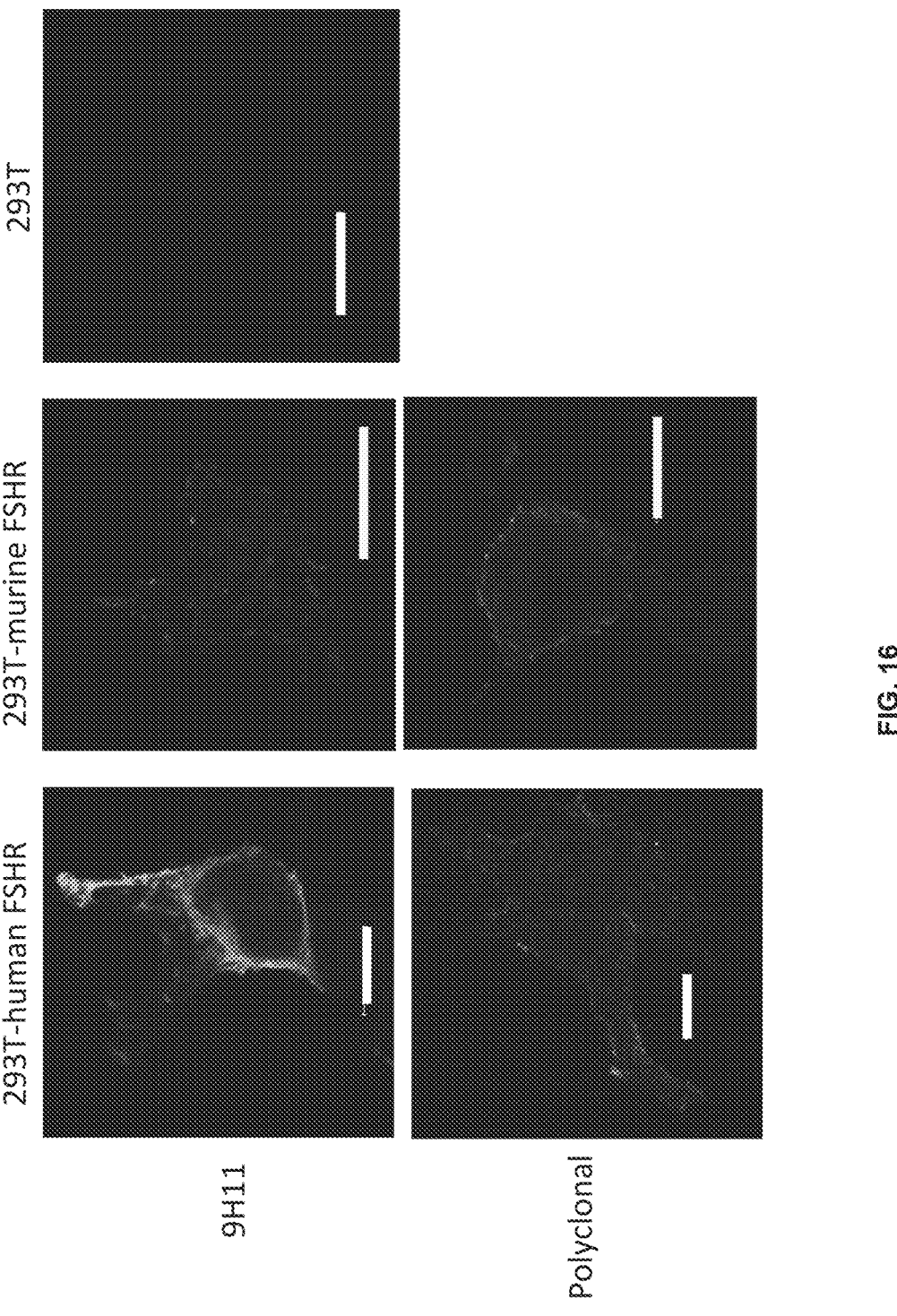

Example 6: 9H11 Detects FSHR by Immunocytochemistry and Immunohistochemistry in Frozen Section The use of 9H11 for staining FSHR in immunocytochemistry through immunofluorescence was validated. To do so, 293T cells were transiently transduced with human or murine FSHR. Immunofluorescence was performed 72 hours after transduction and it was found that 9H11 was able to bind both human and murine FSHR transfected 293T, similar to polyclonal anti-human and anti-mouse FSHR, but not mock transfected (pVax empty vector) 293T (FIG. 16).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated antibody or antigen binding fragment thereof that binds Follicle Stimulating Hormone Receptor (FSHR), wherein the isolated antibody or antigen binding fragment thereof comprises:

A) a heavy chain comprising:

(i) a heavy chain CDR1 having the sequence of SEQ ID NO: 6;

(ii) a heavy chain CDR2 having the sequence of SEQ ID NO: 7; and (iii) a heavy chain CDR3 having the sequence of SEQ ID NO: 8; and B) a light chain comprising:

(i) a light chain CDR1 having the sequence of SEQ ID NO: 2;

(ii) a light chain CDR2 having the sequence of SEQ ID NO: 3; and (iii) a light chain CDR3 having the sequence of SEQ ID NO: 4.

2. The isolated antibody or antigen binding fragment thereof of claim 1, wherein said antibody or antigen binding fragment thereof comprises a heavy chain comprising SEQ ID NO: 5 and a light chain comprising SEQ ID NO: 1.

3. The isolated antibody or antigen binding fragment thereof of claim 1, wherein said antibody or antigen binding fragment thereof is humanized.

4. The isolated humanized antibody or antigen binding fragment thereof of claim 1, wherein said antibody or antigen binding fragment thereof comprises a heavy chain comprising SEQ ID NO: 10 and a light chain comprising SEQ ID NO: 9.

5. The isolated antibody or antigen binding fragment thereof of claim 1, wherein said antibody or antigen binding fragment thereof is chimeric.

6. A recombinant nucleic acid encoding the antibody or antigen binding fragment thereof of claim 1.

7. An antibody-drug conjugate comprising the antibody or antigen binding fragment of claim 1.

8. The antibody-drug conjugate of claim 7, wherein the drug is monomethyl auristatin (EMMAE), ozogamicin, emtansine, amanitin, pyrrolobenzodiazepine (PBD) dimer toxin, a chalichaemicin, a cytotoxic maytansinoid, carboplatin, cisplatin, paclitaxel, vedotin, or diphtheria toxin.

9. A pharmaceutical composition comprising the isolated antibody or antigen binding fragment of claim 1 and a pharmaceutically acceptable carrier.

10. A method of treating a cancer that expresses FSHR in a subject in need thereof, comprising administering to the subject an effective amount of a pharmaceutical composition comprising the isolated antibody or antigen-binding fragment of claim 1, wherein the cancer is ovarian, prostate, breast, colon, pancreas, urinary bladder, kidney, lung, liver, stomach or testis cancer.

11. The method of claim 10, wherein the antibody or antigen binding fragment is administered intravenously, intra-articularly, intraperitoneally, intrathecally, intraventricularly, intrasternally, intracranially, intra-muscularly, subcutaneously, orally or intranasally.

12. The method of claim 10, further comprising administering a second agent to the subject.

13. The method of claim 12, wherein the second agent is at least one of carboplatin, cisplatin, paclitaxel, docetaxel, gemcitabine, bevacizumab, olaparib, rucaparib, niraparib, cyclophosphamide, abiraterone, flutamide, bicalutamide, leuprolide, goserelin, buserelin, triptorelin, degarelix, Enzalutamide, Apalutamide, Sipuleucel-T, Cabazitaxel, Radium-223, trastuzumab, pertuzumab, lapatinib, tamoxifen, oxaliplatin, capecitabine, leucovorin, Irinotecan, Cetuximab, panitumumab, aflibercept, Regorafenib, Trifluridine-tipiracil, immune checkpoint inhibitors, cabozantinib, sunitinib, pazopanib, axitinib, interleukin-2, interferon alpha, mitomycin C, epirubicin, BCG, bleomycin, etoposide, sorafenib, regorafenib, lenvatinib, pemetrexed and/or vinorelbine.

14. The method of claim 10, wherein the cancer is metastatic.

\* \* \* \* \*

SEQUENCE LISTING

```
<160> NUMBER OF SEQ ID NOS: 19

<210> SEQ ID NO 1
<211> LENGTH: 218
<212> TYPE: PRT
<213> ORGANISM: Mus musculus

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
```

```
                20                    25                    30

Gly Ile Ser Phe Leu Asn Trp Phe Gln Gln Lys Pro Gly Gln Pro Pro
        35                    40                    45

Lys Leu Leu Ile Tyr Ala Ala Ser Asn Gln Arg Ser Gly Val Pro Ala
    50                    55                    60

Arg Phe Ser Gly Ser Gly Ser Gly Thr Asp Phe Ser Leu Asn Ile His
65                    70                    75                    80

Pro Met Glu Glu Asp Asp Thr Ala Met Tyr Phe Cys Gln Gln Ser Lys
                85                    90                    95

Glu Val Pro Trp Thr Phe Gly Gly Gly Thr Lys Val Glu Ile Lys Arg
                100                   105                   110

Ala Asp Ala Ala Pro Thr Val Ser Ile Phe Pro Pro Ser Ser Glu Gln
        115                   120                   125

Leu Thr Ser Gly Gly Ala Ser Val Val Cys Phe Leu Asn Asn Phe Tyr
        130                   135                   140

Pro Lys Asp Ile Asn Val Lys Trp Lys Ile Asp Gly Ser Glu Arg Gln
145                   150                   155                   160

Asn Gly Val Leu Asn Ser Trp Thr Asp Gln Asp Ser Lys Asp Ser Ile
                165                   170                   175

Tyr Ser Met Ser Ser Thr Leu Thr Leu Thr Lys Asp Glu Tyr Glu Arg
                180                   185                   190

His Asn Ser Tyr Thr Cys Glu Ala Thr His Lys Thr Ser Thr Ser Pro
        195                   200                   205

Ile Val Lys Ser Phe Asn Arg Asn Glu Cys
    210                   215

<210> SEQ ID NO 2
<211> LENGTH: 15
<212> TYPE: PRT
<213> ORGANISM: Mus musculus

<400> SEQUENCE: 2

Arg Ala Ser Glu Ser Val Asp Asn Tyr Gly Ile Ser Phe Leu Asn
1               5                   10                  15

<210> SEQ ID NO 3
<211> LENGTH: 7
<212> TYPE: PRT
<213> ORGANISM: Mus musculus

<400> SEQUENCE: 3

Ala Ala Ser Asn Gln Arg Ser
1               5

<210> SEQ ID NO 4
<211> LENGTH: 9
<212> TYPE: PRT
<213> ORGANISM: Mus musculus

<400> SEQUENCE: 4

Gln Gln Ser Lys Glu Val Pro Trp Thr
1               5

<210> SEQ ID NO 5
<211> LENGTH: 450
<212> TYPE: PRT
<213> ORGANISM: Mus musculus

<400> SEQUENCE: 5
```

-continued

```
Gln Val Asn Leu Lys Glu Ser Gly Pro Gly Ile Leu Gln Pro Ser Gln
1               5                   10                  15

Thr Leu Asn Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Asp
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Ala Ser Ser Asn Gln Val
65                  70                  75                  80

Phe Leu Lys Ile Ala Ser Val Val Thr Ala Asp Thr Ala Thr Tyr Tyr
                85                  90                  95

Cys Val Gln Ile Asn Tyr Gly Asn Tyr Arg Phe Asp Asn Trp Gly His
            100                 105                 110

Gly Thr Thr Leu Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
```

-continued

```
                 420                 425                 430
Glu Gly Leu His Asn His His Thr Thr Lys Ser Phe Ser Arg Thr Pro
        435                 440                 445

Gly Lys
    450

<210> SEQ ID NO 6
<211> LENGTH: 7
<212> TYPE: PRT
<213> ORGANISM: Mus musculus

<400> SEQUENCE: 6

Thr Ser Gly Met Gly Val Gly
1               5

<210> SEQ ID NO 7
<211> LENGTH: 16
<212> TYPE: PRT
<213> ORGANISM: Mus musculus

<400> SEQUENCE: 7

His Ile Trp Trp Asp Asp Asp Lys Arg Tyr Asn Pro Ala Leu Lys Ser
1               5                   10                  15

<210> SEQ ID NO 8
<211> LENGTH: 10
<212> TYPE: PRT
<213> ORGANISM: Mus musculus

<400> SEQUENCE: 8

Ile Asn Tyr Gly Asn Tyr Arg Phe Asp Asn
1               5                   10

<210> SEQ ID NO 9
<211> LENGTH: 218
<212> TYPE: PRT
<213> ORGANISM: Artificial Sequence
<220> FEATURE:
<223> OTHER INFORMATION: VL-CL (kappa)

<400> SEQUENCE: 9

Asp Ile Gln Met Thr Gln Ser Pro Ser Ser Leu Ser Ala Ser Val Gly
1               5                   10                  15

Asp Arg Val Thr Ile Ser Cys Arg Ala Ser Glu Ser Val Asp Asn Tyr
            20                  25                  30

Gly Ile Ser Phe Leu Asn Trp Phe Gln Gln Lys Pro Gly Lys Ala Pro
        35                  40                  45

Lys Leu Leu Ile Tyr Ala Ala Ser Asn Gln Arg Ser Gly Val Pro Ser
    50                  55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Phe Cys Gln Gln Ser Lys
                85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
```

-continued

```
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 10
<211> LENGTH: 450
<212> TYPE: PRT
<213> ORGANISM: Artificial Sequence
<220> FEATURE:
<223> OTHER INFORMATION: VH-CH1-Hinge Region-CH2-CH3

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ser Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ala His Ile Trp Trp Asp Asp Asp Lys Arg Tyr Asn Pro Ala
    50                  55                  60

Leu Lys Ser Arg Phe Thr Leu Ser Val Asp Arg Ser Lys Asn Thr Leu
65                  70                  75                  80

Tyr Leu Gln Met Asn Ser Leu Arg Ala Glu Asp Thr Ala Thr Tyr Tyr
            85                  90                  95

Cys Val Gln Ile Asn Tyr Gly Asn Tyr Arg Phe Asp Asn Trp Gly His
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

-continued

```
            290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
                325             330             335

Lys Thr Ile Ser Lys Ala Lys Gly Gln Pro Arg Glu Pro Gln Val Tyr
                340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450

<210> SEQ ID NO 11
<211> LENGTH: 697
<212> TYPE: PRT
<213> ORGANISM: Artificial Sequence
<220> FEATURE:
<223> OTHER INFORMATION: Follicule Stimulating Hormone Receptor (FSHR)

<400> SEQUENCE: 11

Met Gly Arg Leu Thr Ser Ser Phe Leu Leu Leu Ile Val Pro Ala Tyr
1               5               10              15

Val Leu Ser Cys His His Arg Ile Cys His Cys Ser Asn Arg Val Phe
                20              25              30

Leu Cys Gln Glu Ser Lys Val Thr Glu Ile Pro Ser Asp Leu Pro Arg
            35              40              45

Asn Ala Ile Glu Leu Arg Phe Val Leu Thr Lys Leu Arg Val Ile Gln
    50              55              60

Lys Gly Ala Phe Ser Gly Phe Gly Asp Leu Glu Lys Ile Glu Ile Ser
65              70              75              80

Gln Asn Asp Val Leu Glu Val Ile Glu Ala Asp Val Phe Ser Asn Leu
                85              90              95

Pro Lys Leu His Glu Ile Arg Ile Glu Lys Ala Asn Asn Leu Leu Tyr
            100             105             110

Ile Asn Pro Glu Ala Phe Gln Asn Leu Pro Asn Leu Gln Tyr Leu Leu
            115             120             125

Ile Ser Asn Thr Gly Ile Lys His Leu Pro Asp Val His Lys Ile His
    130             135             140

Ser Leu Gln Lys Val Leu Leu Asp Ile Gln Asp Asn Ile Asn Ile His
145             150             155             160

Thr Ile Glu Arg Asn Ser Phe Val Gly Leu Ser Phe Glu Ser Val Ile
                165             170             175

Leu Trp Leu Asn Lys Asn Gly Ile Gln Glu Ile His Asn Cys Ala Phe
            180             185             190

Asn Gly Thr Gln Leu Asp Glu Leu Asn Leu Ser Asp Asn Asn Asn Leu
```

-continued

```
                    195                 200                 205

Glu Glu Leu Pro Asn Asp Val Phe His Gly Ala Ser Gly Pro Val Ile
    210                 215                 220

Leu Asp Ile Ser Arg Thr Arg Ile His Ser Leu Pro Ser Tyr Gly Leu
225                 230                 235                 240

Glu Asn Leu Lys Lys Leu Arg Ala Arg Ser Thr Tyr Asn Leu Lys Lys
                245                 250                 255

Leu Pro Thr Leu Glu Lys Leu Val Ala Leu Met Glu Ala Ser Leu Thr
                260                 265                 270

Tyr Pro Ser His Cys Cys Ala Phe Ala Asn Trp Arg Arg Gln Ile Ser
                275                 280                 285

Glu Leu His Pro Ile Cys Asn Lys Ser Ile Leu Arg Gln Glu Val Asp
    290                 295                 300

Tyr Met Thr Gln Ala Arg Gly Gln Arg Ser Ser Leu Ala Glu Asp Asn
305                 310                 315                 320

Glu Ser Ser Tyr Ser Arg Gly Phe Asp Met Thr Tyr Thr Glu Phe Asp
                325                 330                 335

Tyr Asp Leu Cys Asn Glu Val Val Asp Val Thr Cys Ser Pro Lys Pro
                340                 345                 350

Asp Ala Phe Asn Pro Cys Glu Asp Ile Met Gly Tyr Asn Ile Leu Arg
                355                 360                 365

Val Leu Ile Trp Phe Ile Ser Ile Leu Ala Ile Thr Gly Asn Ile Ile
    370                 375                 380

Val Leu Val Ile Leu Thr Thr Ser Gln Tyr Lys Leu Thr Val Pro Arg
385                 390                 395                 400

Phe Leu Met Cys Asn Leu Ala Phe Ala Asp Leu Cys Ile Gly Ile Tyr
                405                 410                 415

Leu Leu Leu Ile Ala Ser Val Asp Ile His Thr Lys Ser Gln Tyr His
                420                 425                 430

Asn Tyr Ala Ile Asp Trp Gln Thr Gly Ala Gly Cys Asp Ala Ala Gly
                435                 440                 445

Phe Phe Thr Val Phe Ala Ser Glu Leu Ser Val Tyr Thr Leu Thr Ala
    450                 455                 460

Ile Thr Leu Glu Arg Trp His Thr Ile Thr His Ala Met Gln Leu Asp
465                 470                 475                 480

Cys Lys Val Gln Leu Arg His Ala Ala Ser Val Met Val Met Gly Trp
                485                 490                 495

Ile Phe Ala Phe Ala Ala Ala Leu Phe Pro Ile Phe Gly Ile Ser Ser
                500                 505                 510

Tyr Met Lys Val Ser Ile Cys Leu Pro Met Asp Ile Asp Ser Pro Leu
                515                 520                 525

Ser Gln Leu Tyr Val Met Ser Leu Leu Val Leu Asn Val Leu Ala Phe
    530                 535                 540

Val Val Ile Cys Gly Cys Tyr Ile His Ile Tyr Leu Thr Val Arg Asn
545                 550                 555                 560

Pro Asn Ile Val Ser Ser Ser Asp Thr Arg Ile Ala Lys Arg Met
                565                 570                 575

Ala Met Leu Ile Phe Thr Asp Phe Leu Cys Met Ala Pro Ile Ser Phe
                580                 585                 590

Phe Ala Ile Ser Ala Ser Leu Lys Val Pro Leu Ile Thr Val Ser Lys
                595                 600                 605

Ala Lys Ile Leu Leu Val Leu Phe His Pro Ile Asn Ser Cys Ala Asn
    610                 615                 620
```

```
Pro Phe Leu Tyr Ala Ile Phe Thr Lys Asn Phe Arg Arg Asp Phe Phe
625             630                 635                 640

Ile Leu Leu Ser Lys Cys Gly Cys Tyr Glu Met Gln Ala Gln Ile Tyr
                645                 650                 655

Arg Thr Glu Thr Ser Ser Thr Val His Asn Thr His Pro Arg Asn Gly
            660                 665                 670

His Cys Ser Ser Ala Pro Arg Val Thr Asn Gly Ser Thr Tyr Ile Leu
        675                 680                 685

Val Pro Leu Ser His Leu Ala Gln Asn
    690                 695

<210> SEQ ID NO 12
<211> LENGTH: 218
<212> TYPE: PRT
<213> ORGANISM: Artificial Sequence
<220> FEATURE:
<223> OTHER INFORMATION: VL-CL (kappa)

<400> SEQUENCE: 12

Asp Ile Gln Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Leu Asn Trp Phe Gln Gln Lys Pro Gly Gln Pro Pro
            35                  40                  45

Lys Leu Leu Ile Tyr Ala Ala Ser Asn Gln Arg Ser Gly Val Pro Ala
    50                  55                  60

Arg Phe Ser Gly Ser Gly Ser Gly Thr Asp Phe Ser Leu Asn Ile His
65              70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 13
<211> LENGTH: 450
<212> TYPE: PRT
<213> ORGANISM: Artificial Sequence
<220> FEATURE:
<223> OTHER INFORMATION: VH-CH1-Hinge Region-CH2-CH3

<400> SEQUENCE: 13

Glu Val Gln Leu Lys Glu Ser Gly Pro Gly Ile Leu Gln Pro Ser Gln
```

-continued

```
1               5              10             15

Thr Leu Asn Leu Thr Cys Ser Phe Ser Gly Phe Ser Leu Ser Thr Ser
            20              25              30

Gly Met Gly Val Gly Trp Ile Arg Gln Pro Ser Gly Lys Gly Leu Asp
            35              40              45

Trp Leu Ala His Ile Trp Trp Asp Asp Asp Lys Arg Tyr Asn Pro Ala
    50              55              60

Leu Lys Ser Arg Leu Thr Ile Ser Lys Asp Ala Ser Ser Asn Gln Val
65              70              75              80

Phe Leu Lys Ile Ala Ser Val Val Thr Ala Asp Thr Ala Thr Tyr Tyr
                85              90              95

Cys Val Gln Ile Asn Tyr Gly Asn Tyr Arg Phe Asp Asn Trp Gly His
                100             105             110

Gly Thr Thr Leu Thr Val Ser Ser Ala Ser Thr Lys Gly Pro Ser Val
                115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
                165             170             175

Leu Gln Ser Ser Gly Leu Tyr Ser Leu Ser Ser Val Val Thr Val Pro
                180             185             190

Ser Ser Ser Leu Gly Thr Gln Thr Tyr Ile Cys Asn Val Asn His Lys
                195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
                245             250             255

Ser Arg Thr Pro Glu Val Thr Cys Val Val Val Asp Val Ser His Glu
                260             265             270

Asp Pro Glu Val Lys Phe Asn Trp Tyr Val Asp Gly Val Glu Val His
                275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
                325             330             335

Lys Thr Ile Ser Lys Ala Lys Gly Gln Pro Arg Glu Pro Gln Val Tyr
                340             345             350

Thr Leu Pro Pro Ser Arg Asp Glu Leu Thr Lys Asn Gln Val Ser Leu
    355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
    420             425             430
```

```
Glu Ala Leu His Asn His Tyr Thr Gln Lys Ser Leu Ser Leu Ser Pro
        435                 440                 445

Gly Lys
    450

<210> SEQ ID NO 14
<211> LENGTH: 238
<212> TYPE: PRT
<213> ORGANISM: Mus musculus

<400> SEQUENCE: 14

Met Glu Lys Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Leu Asn Trp Phe Gln Gln Lys Pro
    50                  55                  60

Gly Gln Pro Pro Lys Leu Leu Ile Tyr Ala Ala Ser Asn Gln Arg Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Val Pro Trp Thr Phe Gly Gly Gly Thr Lys Val
            115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Ile Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
        210                 215                 220

Ser Thr Ser Pro Ile Val Lys Ser Phe Asn Arg Asn Glu Cys
225                 230                 235

<210> SEQ ID NO 15
<211> LENGTH: 469
<212> TYPE: PRT
<213> ORGANISM: Mus musculus

<400> SEQUENCE: 15

Met Gly Arg Leu Thr Ser Ser Phe Leu Leu Leu Ile Val Pro Ala Tyr
1               5                   10                  15

Val Leu Ser Gln Val Asn Leu Lys Glu Ser Gly Pro Gly Ile Leu Gln
            20                  25                  30

Pro Ser Gln Thr Leu Asn Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60
```

-continued

```
Gly Leu Asp Trp Leu Ala His Ile Trp Trp Asp Asp Lys Arg Tyr
65                  70              75              80

Asn Pro Ala Leu Lys Ser Arg Leu Thr Ile Ser Lys Asp Ala Ser Ser
                85              90              95

Asn Gln Val Phe Leu Lys Ile Ala Ser Val Val Thr Ala Asp Thr Ala
            100             105             110

Thr Tyr Tyr Cys Val Gln Ile Asn Tyr Gly Asn Tyr Arg Phe Asp Asn
        115             120             125

Trp Gly His Gly Thr Thr Leu Thr Val Ser Ser Ala Lys Thr Thr Ala
    130             135             140

Pro Ser Val Tyr Pro Leu Ala Pro Val Cys Gly Asp Thr Thr Gly Ser
145             150             155             160

Ser Val Thr Leu Gly Cys Leu Val Lys Gly Tyr Phe Pro Glu Pro Val
            165             170             175

Thr Leu Thr Trp Asn Ser Gly Ser Leu Ser Ser Gly Val His Thr Phe
            180             185             190

Pro Ala Val Leu Gln Ser Asp Leu Tyr Thr Leu Ser Ser Ser Val Thr
            195             200             205

Val Thr Ser Ser Thr Trp Pro Ser Gln Ser Ile Thr Cys Asn Val Ala
    210             215             220

His Pro Ala Ser Ser Thr Lys Val Asp Lys Lys Ile Glu Pro Arg Gly
225             230             235             240

Pro Thr Ile Lys Pro Cys Pro Pro Cys Lys Cys Pro Ala Pro Asn Leu
            245             250             255

Leu Gly Gly Pro Ser Val Phe Ile Phe Pro Pro Lys Ile Lys Asp Val
            260             265             270

Leu Met Ile Ser Leu Ser Pro Ile Val Thr Cys Val Val Val Asp Val
            275             280             285

Ser Glu Asp Asp Pro Asp Val Gln Ile Ser Trp Phe Val Asn Asn Val
    290             295             300

Glu Val His Thr Ala Gln Thr Gln Thr His Arg Glu Asp Tyr Asn Ser
305             310             315             320

Thr Leu Arg Val Val Ser Ala Leu Pro Ile Gln His Gln Asp Trp Met
            325             330             335

Ser Gly Lys Glu Phe Lys Cys Lys Val Asn Asn Lys Asp Leu Pro Ala
            340             345             350

Pro Ile Glu Arg Thr Ile Ser Lys Pro Lys Gly Ser Val Arg Ala Pro
            355             360             365

Gln Val Tyr Val Leu Pro Pro Pro Glu Glu Glu Met Thr Lys Lys Gln
    370             375             380

Val Thr Leu Thr Cys Met Val Thr Asp Phe Met Pro Glu Asp Ile Tyr
385             390             395             400

Val Glu Trp Thr Asn Asn Gly Lys Thr Glu Leu Asn Tyr Lys Asn Thr
            405             410             415

Glu Pro Val Leu Asp Ser Asp Gly Ser Tyr Phe Met Tyr Ser Lys Leu
            420             425             430

Arg Val Glu Lys Lys Asn Trp Val Glu Arg Asn Ser Tyr Ser Cys Ser
            435             440             445

Val Val His Glu Gly Leu His Asn His His Thr Thr Lys Ser Phe Ser
    450             455             460

Arg Thr Pro Gly Lys
465
```

-continued

```
<210> SEQ ID NO 16
<211> LENGTH: 236
<212> TYPE: PRT
<213> ORGANISM: Artificial Sequence
<220> FEATURE:
<223> OTHER INFORMATION: Signal peptide-VL-CL (kappa)

<400> SEQUENCE: 16

Met Asp Trp Thr Trp Ile Leu Phe Leu Val Ala Ala Ala Thr Arg Val
1               5                   10                  15

His Ser Asp Ile Gln Met Thr Gln Ser Pro Ser Ser Leu Ser Ala Ser
            20                  25                  30

Val Gly Asp Arg Val Thr Ile Ser Cys Arg Ala Ser Glu Ser Val Asp
            35                  40                  45

Asn Tyr Gly Ile Ser Phe Leu Asn Trp Phe Gln Gln Lys Pro Gly Lys
        50                  55                  60

Ala Pro Lys Leu Leu Ile Tyr Ala Ala Ser Asn Gln Arg Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Phe Cys Gln Gln
            100                 105                 110

Ser Lys Glu Val Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 17
<211> LENGTH: 468
<212> TYPE: PRT
<213> ORGANISM: Artificial Sequence
<220> FEATURE:
<223> OTHER INFORMATION: Signal peptide-VH-CH1-Hinge Region-CH2-CH3

<400> SEQUENCE: 17

Met Asp Trp Thr Trp Ile Leu Phe Leu Val Ala Ala Ala Thr Arg Val
1               5                   10                  15

His Ser Glu Val Gln Leu Val Glu Ser Gly Gly Gly Leu Val Gln Pro
            20                  25                  30

Gly Gly Ser Leu Arg Leu Ser Cys Ser Phe Ser Gly Phe Ser Leu Ser
            35                  40                  45

Thr Ser Gly Met Gly Val Gly Trp Ile Arg Gln Ala Pro Gly Lys Gly
        50                  55                  60

Leu Glu Trp Val Ala His Ile Trp Trp Asp Asp Asp Lys Arg Tyr Asn
65                  70                  75                  80
```

```
Pro Ala Leu Lys Ser Arg Phe Thr Leu Ser Val Asp Arg Ser Lys Asn
            85                  90                  95

Thr Leu Tyr Leu Gln Met Asn Ser Leu Arg Ala Glu Asp Thr Ala Thr
            100                 105                 110

Tyr Tyr Cys Val Gln Ile Asn Tyr Gly Asn Tyr Arg Phe Asp Asn Trp
            115                 120                 125

Gly His Gly Thr Leu Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 18
<211> LENGTH: 236
```

-continued

```
<212> TYPE: PRT
<213> ORGANISM: Artificial Sequence
<220> FEATURE:
<223> OTHER INFORMATION: Signal peptide-VL-CL (kappa)

<400> SEQUENCE: 18

Met Asp Trp Thr Trp Ile Leu Phe Leu Val Ala Ala Ala Thr Arg Val
1               5                   10                  15

His Ser Asp Ile Gln Met Thr Gln Ser Pro Ala Ser Leu Ala Val Ser
            20                  25                  30

Leu Gly Gln Arg Ala Thr Ile Ser Cys Arg Ala Ser Glu Ser Val Asp
        35                  40                  45

Asn Tyr Gly Ile Ser Phe Leu Asn Trp Phe Gln Gln Lys Pro Gly Gln
    50                  55                  60

Pro Pro Lys Leu Leu Ile Tyr Ala Ala Ser Asn Gln Arg Ser Gly Val
65                  70                  75                  80

Pro Ala Arg Phe Ser Gly Ser Gly Ser Gly Thr Asp Phe Ser Leu Asn
                85                  90                  95

Ile His Pro Met Glu Glu Asp Asp Thr Ala Met Tyr Phe Cys Gln Gln
            100                 105                 110

Ser Lys Glu Val Pro Trp Thr Phe Gly Gly Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 19
<211> LENGTH: 468
<212> TYPE: PRT
<213> ORGANISM: Artificial Sequence
<220> FEATURE:
<223> OTHER INFORMATION: Signal peptide-VH-CH1-Hinge Region-CH2-CH3

<400> SEQUENCE: 19

Met Asp Trp Thr Trp Ile Leu Phe Leu Val Ala Ala Ala Thr Arg Val
1               5                   10                  15

His Ser Glu Val Gln Leu Lys Glu Ser Gly Pro Gly Ile Leu Gln Pro
            20                  25                  30

Ser Gln Thr Leu Asn Leu Thr Cys Ser Phe Ser Gly Phe Ser Leu Ser
        35                  40                  45

Thr Ser Gly Met Gly Val Gly Trp Ile Arg Gln Pro Ser Gly Lys Gly
    50                  55                  60

Leu Asp Trp Leu Ala His Ile Trp Trp Asp Asp Asp Lys Arg Tyr Asn
65                  70                  75                  80

Pro Ala Leu Lys Ser Arg Leu Thr Ile Ser Lys Asp Ala Ser Ser Asn
                85                  90                  95
```

-continued

```
Gln Val Phe Leu Lys Ile Ala Ser Val Val Thr Ala Asp Thr Ala Thr
            100             105             110

Tyr Tyr Cys Val Gln Ile Asn Tyr Gly Asn Tyr Arg Phe Asp Asn Trp
            115             120             125

Gly His Gly Thr Thr Leu Thr Val Ser Ser Ala Ser Thr Lys Gly Pro
            130             135             140

Ser Val Phe Pro Leu Ala Pro Ser Ser Lys Ser Thr Ser Gly Gly Thr
145             150             155             160

Ala Ala Leu Gly Cys Leu Val Lys Asp Tyr Phe Pro Glu Pro Val Thr
                165             170             175

Val Ser Trp Asn Ser Gly Ala Leu Thr Ser Gly Val His Thr Phe Pro
            180             185             190

Ala Val Leu Gln Ser Ser Gly Leu Tyr Ser Leu Ser Ser Val Val Thr
            195             200             205

Val Pro Ser Ser Ser Leu Gly Thr Gln Thr Tyr Ile Cys Asn Val Asn
    210             215             220

His Lys Pro Ser Asn Thr Lys Val Asp Lys Lys Val Glu Pro Lys Ser
225             230             235             240

Cys Asp Lys Thr His Thr Cys Pro Pro Cys Pro Ala Pro Glu Leu Leu
            245             250             255

Gly Gly Pro Ser Val Phe Leu Phe Pro Pro Lys Pro Lys Asp Thr Leu
            260             265             270

Met Ile Ser Arg Thr Pro Glu Val Thr Cys Val Val Val Asp Val Ser
            275             280             285

His Glu Asp Pro Glu Val Lys Phe Asn Trp Tyr Val Asp Gly Val Glu
            290             295             300

Val His Asn Ala Lys Thr Lys Pro Arg Glu Glu Gln Tyr Asn Ser Thr
305             310             315             320

Tyr Arg Val Val Ser Val Leu Thr Val Leu His Gln Asp Trp Leu Asn
                325             330             335

Gly Lys Glu Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Lys Asn Gln Val
    370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
            405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
    450             455             460

Ser Pro Gly Lys
465
```